United States Patent
Yamaguchi et al.

(10) Patent No.: US 7,270,415 B2
(45) Date of Patent: Sep. 18, 2007

(54) RETINA OBSERVATION APPARATUS AND RETINA OBSERVATION METHOD

(75) Inventors: Tatsuo Yamaguchi, Tokyo (JP); Toshifumi Mihashi, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 121 days.

(21) Appl. No.: 10/554,944

(22) PCT Filed: Apr. 22, 2004

(86) PCT No.: PCT/JP2004/005791

§ 371 (c)(1), (2), (4) Date: Nov. 30, 2005

(87) PCT Pub. No.: WO2004/096034

PCT Pub. Date: Nov. 11, 2004

(65) Prior Publication Data

US 2007/0030447 A1    Feb. 8, 2007

(30) Foreign Application Priority Data

Apr. 30, 2003   (JP) ............................. 2003-125279

(51) Int. Cl. *A61B 3/10* (2006.01)
(52) U.S. Cl. ...................... 351/221; 351/246
(58) Field of Classification Search ................ 351/221, 351/246, 205, 200, 211, 212
See application file for complete search history.

(56) References Cited

U.S. PATENT DOCUMENTS 6,695,450 B2 * 2/2004 Hirohara et al. ............ 351/211

FOREIGN PATENT DOCUMENTS

| JP | 2001-095760 A | 4/2001 |
| JP | 2001-507258 A | 6/2001 |
| JP | 2002-209854 A | 7/2002 |
| JP | 2003-111729 A | 4/2003 |
| JP | 2003-116792 A | 4/2003 |
| WO | WO 01/47407 A1 | 7/2001 |

OTHER PUBLICATIONS

H. Uozato, "Ophthalmology Application of Adaptive Optics, Practical Ophthalmology", 2001, vol. 4, No. 6, p. 114-116.

* cited by examiner

*Primary Examiner*—Hung Xuan Dang
(74) *Attorney, Agent, or Firm*—Foley & Lardner LLP

(57) ABSTRACT

It is possible to improve the quality of an image of an eyeground, thereby acquiring an optimal image. An eyeground observation system (3) acquires an eyeground image via a compensation optical section (70) correcting the image of the eyeground obtained by illumination of an eyeground illumination system (2). A wave front correction system (1) measures wave front measurement data including a wave front aberration of the eye to be checked and/or aberration to be corrected, thereby acquiring the optical characteristic of the eye to be checked. An image data formation section (14-2) performs simulation of viewing at the eyeground, thereby calculating the simulation image data or MTF data. A correction amount decision section (14-3) decides a correction amount according to a voltage change template stored in a memory (14-4) and outputs it to a control section (15). Moreover, the correction amount decision section (14-3) uses the simulation result for a plurality of voltage change templates so as to calculate a value indicating the matching degree of the pattern or MTF data corresponding to a spatial frequency of cells of the eyeground and decide an appropriate correction amount

26 Claims, 19 Drawing Sheets

EXAMPLE OF ARRANGEMENT OF MOVING ELEMENTS

| ELEMENT NUMBER | 1 | 2 | 3 | 4 | 5 | 6 | 7 | 8 | 9 | 10 | 11 | 12 | ... | 33 | 34 | 35 | 36 | 37 |
|---|---|---|---|---|---|---|---|---|---|---|---|---|---|---|---|---|---|---|
| VOLTAGE $V_i$ | $V_1$ | $V_2$ | $V_3$ | $V_4$ | $V_5$ | $V_6$ | $V_7$ | $V_8$ | $V_9$ | $V_{10}$ | $V_{11}$ | $V_{12}$ | ... | $V_{33}$ | $V_{34}$ | $V_{35}$ | $V_{36}$ | $V_{37}$ |

REFERENCE VOLTAGE ASSIGNED TO EACH ELEMENT

FIG. 3

| TEMPLATE NUMBER \ ELEMENT NUMBER | 1 | 2 | 3 | 4 | 5 | 6 | 7 | 8 | 9 | 10 | 11 | 12 | ... | 33 | 34 | 35 | 36 | 37 |
|---|---|---|---|---|---|---|---|---|---|---|---|---|---|---|---|---|---|---|
| 1 | 0.0 | 0.0 | 0.0 | 0.0 | 0.0 | 0.0 | 0.0 | 0.0 | 0.0 | 0.0 | 0.0 | 0.0 | | 0.0 | 0.0 | 0.0 | 0.0 | 0.0 |
| 2 | 0.5 | -0.1 | -0.1 | -0.1 | -0.1 | -0.1 | -0.1 | 0.5 | 0.5 | 0.5 | 0.5 | 0.5 | | 0.05 | 0.05 | 0.05 | 0.05 | 0.05 |
| 3 | -0.5 | 0.1 | 0.1 | 0.1 | 0.1 | 0.1 | 0.1 | -0.5 | -0.5 | -0.5 | -0.5 | -0.5 | | -0.05 | -0.05 | -0.05 | -0.05 | -0.05 |
| 4 | 0.0 | 0.5 | 0.5 | 0.5 | 0.5 | 0.5 | 0.5 | 0.1 | 0.1 | 0.1 | 0.1 | 0.1 | | 0.0 | 0.0 | 0.0 | 0.0 | 0.0 |
| 5 | 0.0 | -0.5 | -0.5 | -0.5 | -0.5 | -0.5 | -0.5 | -0.1 | -0.1 | -0.1 | -0.1 | -0.1 | | 0.0 | 0.0 | 0.0 | 0.0 | 0.0 |
| 6 | 0.25 | 0.4 | 0.4 | 0.4 | 0.4 | 0.4 | 0.5 | -0.5 | -0.5 | -0.5 | -0.5 | -0.5 | | 0.1 | 0.1 | 0.1 | 0.1 | 0.1 |
| 7 | -0.25 | -0.4 | -0.4 | -0.4 | -0.4 | -0.4 | -0.5 | 0.5 | 0.5 | 0.5 | 0.5 | 0.5 | | -0.1 | -0.1 | -0.1 | -0.1 | -0.1 |
| 8 | 0.2 | 0.0 | 0.0 | 0.0 | 0.0 | 0.0 | 0.0 | -0.05 | -0.05 | -0.05 | -0.05 | -0.05 | | -0.05 | -0.05 | -0.05 | -0.05 | -0.05 |
| 9 | -0.2 | 0.0 | 0.0 | 0.0 | 0.0 | 0.0 | 0.0 | 0.05 | 0.05 | 0.05 | 0.05 | 0.05 | | 0.05 | 0.05 | 0.05 | 0.05 | 0.05 |

EXAMPLE OF CONCENTRIC TEMPLATES (ELEMENT COUNT n = 37, TEMPLATE COUNT m = 9)

FIG. 4

| Template \ Element | 1 | 2 | 3 | 4 | 5 | 6 | 7 | 8 | 9 | 10 | 11 | 12 | ... | 33 | 34 | 35 | 36 | 37 |
|---|---|---|---|---|---|---|---|---|---|---|---|---|---|---|---|---|---|---|
| 1 | 0.0 | 0.0 | 0.0 | 0.0 | 0.0 | 0.0 | 0.0 | 0.0 | 0.0 | 0.0 | 0.0 | 0.0 | | 0.0 | 0.0 | 0.0 | 0.0 | 0.0 |
| 2 | 0.25 | -0.2 | -0.15 | -0.18 | -0.2 | -0.15 | -0.18 | 0.15 | 0.25 | -0.05 | 0.1 | 0.0 | | 0.15 | 0.1 | 0.0 | 0.0 | 0.05 |
| 3 | -0.25 | 0.2 | 0.15 | 0.18 | 0.2 | 0.15 | 0.18 | -0.15 | -0.25 | 0.05 | -0.1 | 0.0 | | -0.15 | -0.1 | 0.0 | 0.0 | -0.05 |
| 4 | 0.05 | -0.25 | -0.1 | -0.25 | -0.25 | -0.1 | -0.25 | 0.2 | 0.1 | 0.0 | -0.25 | 0.1 | | 0.1 | 0.0 | 0.15 | 0.2 | 0.0 |
| 5 | -0.05 | 0.25 | 0.1 | 0.25 | 0.25 | 0.1 | 0.25 | -0.2 | -0.1 | 0.0 | 0.25 | -0.1 | | -0.1 | 0.0 | -0.15 | -0.2 | 0.0 |
| 6 | 0.0 | 0.05 | 0.15 | 0.1 | 0.05 | 0.15 | 0.1 | 0.2 | 0.2 | 0.05 | 0.2 | 0.15 | | 0.0 | 0.05 | 0.0 | -1.0 | -0.05 |
| 7 | 0.0 | -0.05 | -0.15 | -0.1 | -0.05 | -0.15 | -0.1 | -0.2 | -0.2 | -0.05 | -0.2 | -0.15 | | 0.0 | -0.05 | 0.0 | 1.0 | 0.05 |
| 8 | 0.15 | 0.15 | 0.25 | 0.3 | 0.15 | 0.25 | 0.3 | -0.15 | -0.25 | -0.3 | 0.0 | -0.15 | | 0.15 | 0.1 | 0.5 | 0.0 | -0.5 |
| 9 | -0.15 | -0.15 | -0.25 | -0.3 | -0.15 | -0.25 | -0.3 | 0.15 | 0.25 | 0.3 | 0.0 | 0.15 | | -0.15 | -0.1 | -0.5 | 0.0 | 0.5 |

ELEMENT NUMBER

TEMPLATE NUMBER

EXAMPLE OF SYMMETRIC TEMPLATES (ELEMENT COUNT n = 37, TEMPLATE COUNT m = 9)

FIG. 5

| TEMPLATE NUMBER \ ELEMENT NUMBER | 1 | 2 | 3 | 4 | 5 | 6 | 7 | 8 | 9 | 10 | 11 | 12 | ... | 33 | 34 | 35 | 36 | 37 |
|---|---|---|---|---|---|---|---|---|---|---|---|---|---|---|---|---|---|---|
| 1 | 0.0 | 0.0 | 0.0 | 0.0 | 0.0 | 0.0 | 0.0 | 0.0 | 0.0 | 0.0 | 0.0 | 0.0 | | 0.0 | 0.0 | 0.0 | 0.0 | 0.0 |
| 2 | 0.25 | 0.2 | 0.15 | 0.18 | -0.2 | -0.15 | -0.18 | -0.15 | -0.25 | 0.05 | -0.1 | 0.0 | | 0.15 | 0.1 | 0.0 | 0.0 | 0.05 |
| 3 | -0.25 | -0.2 | -0.15 | -0.18 | 0.2 | 0.15 | 0.18 | 0.15 | 0.25 | -0.05 | 0.1 | 0.0 | | -0.15 | -0.1 | 0.0 | 0.0 | -0.05 |
| 4 | 0.05 | 0.25 | 0.1 | 0.25 | -0.25 | -0.1 | -0.25 | -0.2 | -0.1 | 0.0 | 0.25 | -0.1 | | 0.1 | 0.0 | 0.15 | 0.2 | 0.0 |
| 5 | -0.05 | -0.25 | -0.1 | -0.25 | 0.25 | 0.1 | 0.25 | 0.2 | 0.1 | 0.0 | -0.25 | -0.1 | | -0.1 | 0.0 | -0.15 | -0.2 | 0.0 |
| 6 | 0.0 | -0.05 | -0.15 | -0.1 | 0.05 | 0.15 | 0.1 | 0.2 | -0.2 | -0.05 | -0.2 | -0.15 | | 0.0 | 0.05 | 0.0 | -1.0 | -0.05 |
| 7 | 0.0 | 0.05 | 0.15 | 0.1 | -0.05 | -0.15 | -0.1 | -0.2 | 0.2 | 0.05 | 0.2 | 0.15 | | 0.0 | -0.05 | 0.0 | 1.0 | 0.05 |
| 8 | 0.15 | -0.15 | 0.15 | -0.3 | 0.15 | 0.25 | 0.3 | 0.15 | 0.25 | 0.3 | 0.0 | 0.15 | | 0.15 | 0.1 | 0.5 | 0.0 | -0.5 |
| 9 | -0.15 | 0.15 | 0.25 | 0.3 | -0.15 | -0.25 | -0.3 | -0.15 | -0.25 | -0.3 | 0.0 | -0.15 | | -0.15 | -0.1 | -0.5 | 0.0 | 0.5 |

EXAMPLE OF ASYMMETRIC TEMPLATES (ELEMENT COUNT n = 37, TEMPLATE COUNT m = 9)

FIG. 6

| TEMPLATE NUMBER | | $V_1$ | $V_2$ | $V_3$ | | $V_{37}$ | MATCHING VALUE |
|---|---|---|---|---|---|---|---|
| | 1 | 200.05 | 198.15 | 205.05 | | 105.05 | 0.875 |
| | 2 | 199.75 | 198.13 | 205.02 | | 105.10 | 0.887 |
| | 3 | 199.85 | 198.15 | 204.25 | | 104.75 | 0.867 |
| | 4 | 199.80 | 197.70 | 204.50 | | 105.15 | 0.855 |
| | 5 | 199.70 | 198.30 | 205.10 | | 105.10 | 0.899 |
| | 6 | 199.75 | 198.25 | 205.15 | | 104.95 | 0.883 |
| | 7 | 199.75 | 197.90 | 205.05 | | 104.80 | 0.901 |
| | 8 | 199.80 | 198.05 | 205.10 | | 105.05 | 0.845 |
| | 9 | 200.00 | 198.15 | 204.95 | | 105.00 | 0.877 |
| | 10 | 199.95 | 198.05 | 205.00 | | 105.05 | 0.865 |

SAMPLE FORMAT OF VOLTAGE VALUES AND MATCHING VALUE

FIG. 7

FIG. 9  <VOLTAGE-CHANGE TEMPLATE SELECTION>

PATTERN ORIGINAL IMAGES Pat(x,y)
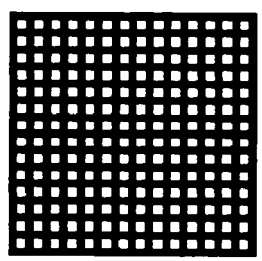 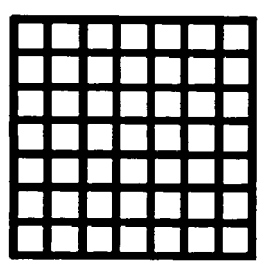 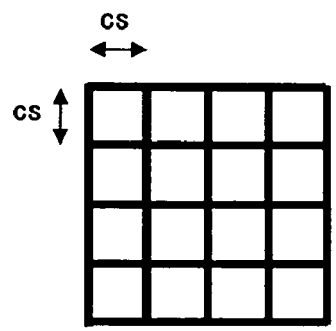
SMALL CELL SIZE        MEDIUM CELL SIZE        LARGE CELL SIZE
FIG. 17

PATTERN TEMPLATE IMAGES PT(x,y)
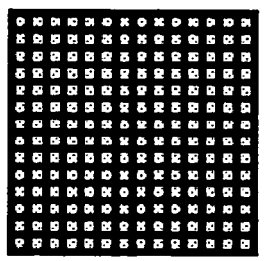
SMALL CELL SIZE
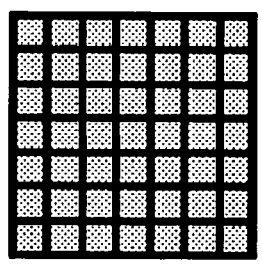
MEDIUM CELL SIZE
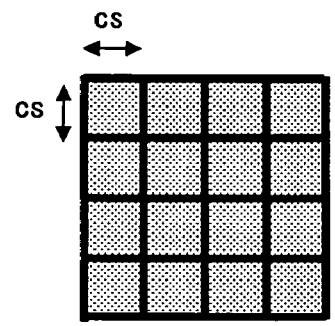
LARGE CELL SIZE
FIG. 18

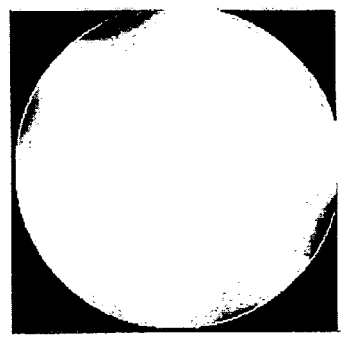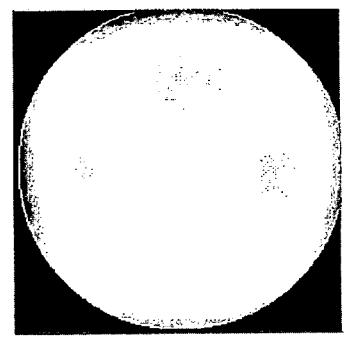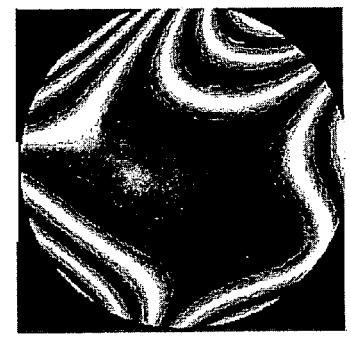
FIG. 19

RETINA OBSERVATION APPARATUS AND RETINA OBSERVATION METHOD

TECHNICAL FIELD

The present invention relates to retina observation apparatuses and retina observation methods, and more specifically, to an retina observation apparatus and an retina observation method that allow the aberration of an eye under examination to be corrected by means of a compensating optical device and allow observations to be made up to the cell level.

BACKGROUND ART

In the conventional retina observation, the retina of an eye under examination has been observed with the aberration of the eye minimized. There have been disclosed a method and an apparatus of improving the eyesight and the resolution of an image on the retina by deforming an optical correcting member like a deformable mirror (see, for example, patent document 1). In the apparatus, a Hartmann-Shack wavefront sensor determines the wavefront aberration value of the eye, and the deformable mirror is deformed to correct the aberration value accordingly. The process of deforming the deformable mirror is repeated until the RMS of error in the determined wavefront aberration reaches the asymptotic value, and the deformable mirror is deformed to an appropriate shape for providing a wavefront for correcting the aberration of the eye.

Patent Document 1

PCT International Patent Application Publication No. 2001-507258

DISCLOSURE OF INVENTION

The compensating optical device (such as the deformable mirror) would not correct the aberration completely and would sometimes leave a great aberration. It is preferable that the RMS of the remaining aberration do not exceed 0.08 times the wavelength (practically no aberration). Some low-cost compensating optical devices for a human eye may leave an aberration of about 0.2 times the wavelength. A remaining aberration of that level has made it difficult to improve the picture quality of the retina image. Even if the deformation of the compensating optical device brings the RMS of error to the level of the asymptotic value, the remaining aberration may hinder an optimum image from being obtained.

The present invention addresses the problems described above, with an object of adjusting the correction to be made by the compensating optical device so that the quality of the retina image is improved and obtaining an appropriate amount of correction. Another object of the present invention is to obtain an appropriate amount of correction for improving the picture quality in accordance with a value obtained from pattern matching between the manner in which a visual target is perceived by an eye under examination and a certain pattern template, or an MTF (modulation transfer function). A further object of the present invention is to provide an retina image corrected by an appropriate correction amount. A still another object of the present invention is to improve the quality of the retina image by means of a voltage-change template provided to adjust the correction amount of the compensating optical device. A still further object of the present invention is to evaluate the image quality in consideration of the size of the retina cell and to enable observations up to the cell level.

According to a first solving means of this invention, there is provided an retina observation apparatus comprising:

an retina illumination unit for illuminating the retina of an eye under examination for the purpose of observation;

a compensating optical section for correcting a image of the retina formed by the illumination of the retina illumination unit by a given amount of correction;

an retina-image-forming optical block for forming an retina image by receiving the image of the retina corrected by the compensating optical section;

an retina-image-light-receiving section for receiving the retina image formed by the retina-image-forming optical block;

a wavefront measurement block for obtaining wavefront measurement data including at least either or both of a wavefront aberration of the eye under examination and the aberration corrected by the compensating optical section;

an optical characteristics measurement block for obtaining optical characteristics including a high-order aberration of the eye under examination, from the wavefront measurement data given by the wavefront measurement block;

an image data formation block for simulating the manner in which a visual target is perceived on the retina, in accordance with the optical characteristics obtained by the optical characteristics measurement block, and calculating data indicating the manner of perception;

a storage block for storing a plurality of voltage-change templates for use in an adjustment of the compensating optical section; and a correction amount determination block for selecting a voltage-change template stored in the storage block, determining an amount of correction to be made by the compensating optical section in accordance with the template and outputting the amount of correction to the compensating optical section, obtaining evaluation data for evaluating the quality of the image in accordance with the data indicating the manner in which the visual target is perceived, obtained by the image data formation block, in consideration of the amount of correction based on the plurality of voltage-change templates, determining an appropriate amount of correction to be made by the compensating optical section in accordance with the evaluation data, and outputting the appropriate amount of correction to the compensating optical section.

According to a second solving means of this invention, there is provided an retina observation method comprising:

a step of illuminating the retina of an eye under examination for the purpose of observation;

a step of correcting a image of the retina formed by the illumination, by a given amount of correction;

a step of forming an retina image by receiving the corrected image of the retina;

a step of measuring wavefront measurement data indicating at least either or both of a wavefront aberration of the eye under examination and the aberration to be corrected;

a step of obtaining optical characteristics including a high-order aberration of the eye under examination, from the wavefront measurement data;

a step of calculating data indicating the manner of perception, by simulating the manner in which a image is perceived on the retina, in accordance with the obtained optical characteristics;

a step of determining and outputting the amount of correction in accordance with the template which is selected a voltage-change template for use in an adjustment of an amount of correction and;

a step of determining an appropriate amount of correction in accordance with the evaluation data which is obtained for evaluating the quality of the image in accordance with the data indicating the manner in which the image is perceived, in consideration of the amount of correction based on a plurality of voltage-change templates and a step of outputting the amount of correction determined in the step of determing.

BRIEF DESCRIPTION OF THE DRAWINGS

FIG. 3 shows the format of a reference voltage table for storing a reference voltage of a voltage change.

FIG. 4 shows the format of a table of concentric templates.

FIG. 5 shows the format of a table of symmetric templates.

FIG. 6 shows the format of a table of asymmetric templates.

FIG. 7 shows a format of template matching, including matching values.

FIG. 17 is a view illustrating pattern original images.

FIG. 18 is a view illustrating pattern template images PT(x,y).

FIG. 19 is a view comparing an image obtained through pattern optimization with other images.

BEST MODE FOR CARRYING OUT THE INVENTION

1. Hardware Configuration

Figure 1:
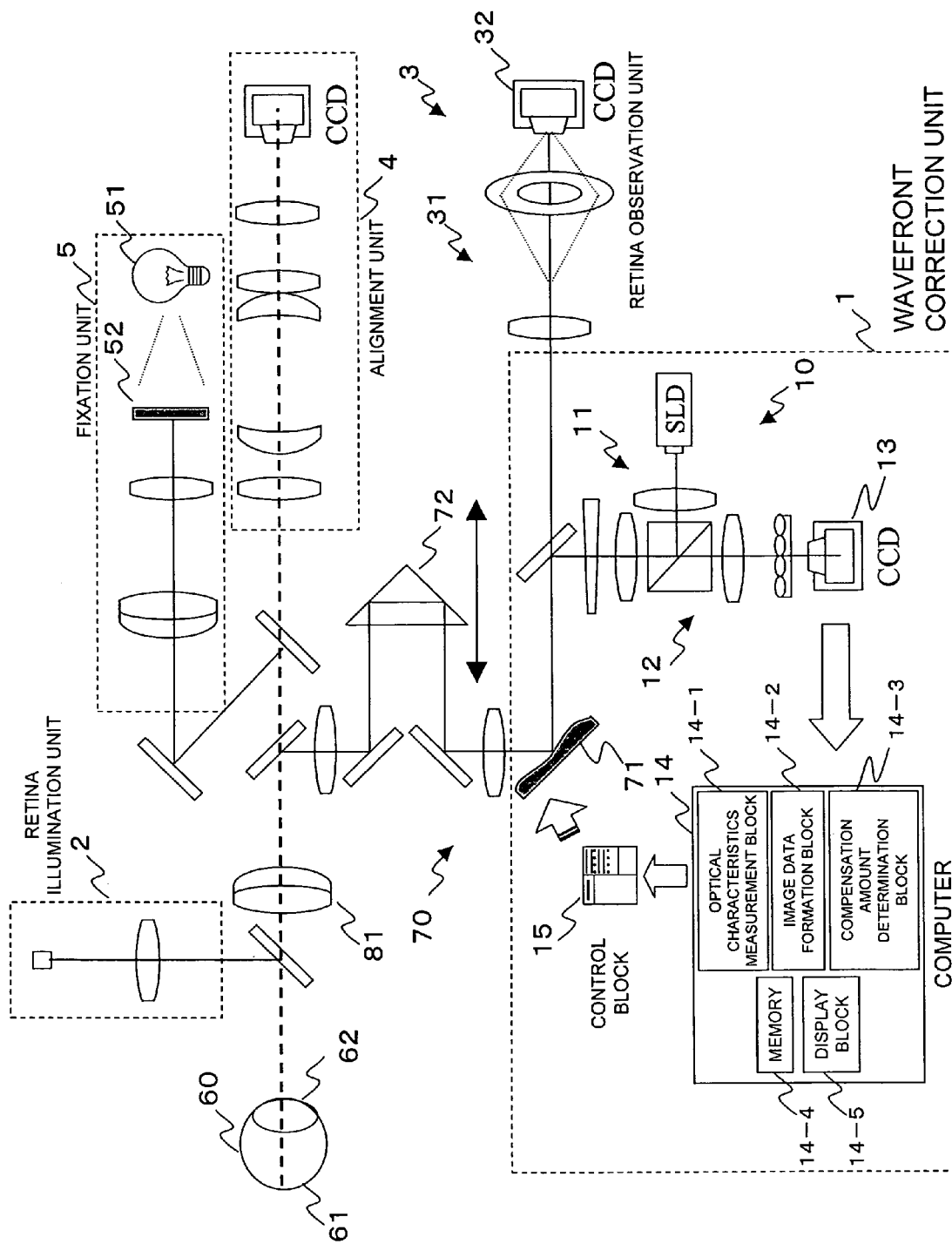
FIG. 1 is a diagram showing the configuration of an retina observation apparatus.

FIG. 1 is a diagram showing the configuration of an retina observation apparatus. The retina observation apparatus includes a wavefront correction unit 1, an retina illumination unit 2, an retina observation unit 3, an alignment unit 4, a fixation unit 5, and a compensating optical section 70. The wavefront correction unit 1 includes a point-image-projecting optical block 11, a point-image-light-receiving optical block 12, a wavefront measurement block 10 containing a point-image-light-receiving section 13, a computer 14, and a control block 15. The retina observation unit 3 includes an retina-image-forming optical block 31 and an retina-image-light-receiving section 32. The computer 14 includes an optical characteristics measurement block 14-1, an image data formation block 14-2, a compensation amount determination block 14-3, and a memory 14-4. The computer 14 may also include a display block 14-5, an input block, and the like. The figure shows the retina (retina) 61 and the cornea (anterior) 62 of an eye under examination 60.

The first illumination optical block (point-image-projecting optical block) 11 contains, for example, a first light source, and illuminates a minute area on the retina of the eye under examination with a light beam from the first light source. The first illumination optical system 11 also contains a condenser lens and a relay lens, for instance.

It is preferable that the first light source have a high spatial coherence and a low time coherence. The first light source in this embodiment is a super luminescence diode (SLD), which provides a high-intensity point light source. The first light source is not necessarily the SLD, and a device having a high spatial coherence and a high time coherence, such as a laser device, can also be used if the time coherence is appropriately lowered by inserting a rotating diffuser or the like. A device not having a high spatial coherence nor having a high time coherence, such as an LED, can be used by providing a pinhole or the like in the position of the light source in the optical path, if the amount of light is sufficient. The first wavelength of the first light source for illumination can be an infrared wavelength of 780 nm, for instance.

The first light-receiving optical block (point-image-light-receiving optical block) 12 receives a light beam reflected back from the retina of an eye under examination and guides the light beam to the first light-receiving section (point-image-light-receiving section) 13. The first light-receiving optical block 12 includes a relay lens, a beam splitter, and a conversion member (splitting element) for converting a reflected light beam to at least seventeen beams. The beam splitter includes a mirror (polarizing beam splitter, for instance) for reflecting the light beam coming from the first light source and passing the light beam which has been returning through an afocal lens 81 after being reflected by the retina of the eye under examination 60. The conversion member is a wavefront conversion member for converting the reflected light beam to a plurality of beams. The conversion member can be a plurality of micro-Fresnel lenses disposed in a plane orthogonal to the optical axis. The light reflected from the retina 61 is gathered through the conversion member onto the first light-receiving section 13.

The first light-receiving section 13 receives light from the first light-receiving optical block 12 through the conversion member and generates a first signal. The front focal point of the afocal lens 81 approximately agrees with the pupil of the eye under examination 60.

The first illumination optical block 11 and the first light-receiving optical block 12 keep such a relationship that the peak of the signal generated from the reflected light by the first light-receiving section 13 is maximized, on the assumption that the light is reflected at a point where light beams from the first light source gather, and a prism 72 can move in such a direction that the peak of the signal generated by the first light-receiving section 13 increases and can stop in a position where the intensity is maximized. As a result, the light beam from the first light source gathers onto the eye under examination.

The second illumination optical unit (retina illumination unit) 2 includes, for example, a second light source, a condenser lens, and a beam splitter, and illuminates a certain region on the retina of the eye under examination with a second light beam coming from the second light source. The second light source emits a red light beam having a second wavelength of 630 nm, for instance. The second light source is a point light source or an area light source for the retina 61 and can be in the red region. The wavelength can be appropriately selected: for instance, the first light source for Hartmann measurement has a wavelength of 840 nm, and the light source for lighting the anterior, not shown, has wavelengths of 850 to 930 nm (860 to 880 nm at present) in the infrared or near-infrared region. The beam splitter can be a polarizing beam splitter for reflecting a light beam coming from the second light source and passing a light beam reflected back from the eye under examination 60.

Illumination on the retina 61 may be provided by a mirror with an opening, for instance, and may be limited to the observation area of the retina 61. The mirror with an opening and the pupil should conjugate to avoid reflection at the top of the cornea. Alternatively, a ring-shaped aperture having 100% transmittance at the center and 10% transmittance in the periphery, for instance, may be used to illuminate the whole of the retina 61.

The second light-receiving optical block (retina-image-forming optical block) 31 includes, for instance, the afocal lens 81, the compensating optical section 70, a beam splitter, and a condenser lens. The second light-receiving optical block guides light with a second wavelength reflected by the retina 61, through the compensating optical section 70 to the second light-receiving section (retina-image-light-receiving section) 32. The beam splitter includes, for instance, a dichroic mirror which reflects a light beam with the first wavelength and passes a light beam with the second wavelength. The second light-receiving section 32 receives the retina image formed by the second light-receiving optical block 31 and generates a second signal. The second light-receiving section 32 can also be formed by a light-receiving element having a sensitivity to the second wavelength (red light).

The compensating optical section 70 includes a compensating optical device 71 such as adaptive optics for compensating for aberration of measured light and either or both of a spherical lens and a moving prism 72 for correcting a spherical component while moving in the direction of the optical axis. The compensating optical section 70 is disposed in the first light-receiving optical block 12 and the second light-receiving optical block 31 and compensates for aberration of a light beam reflected from the eye under examination 60. The compensating optical section 70 may also compensate for aberration of the light beam emitted from the first light source, so that a minute area on the retina of an eye under examination can be illuminated by the aberration-compensated light beam.

As the compensating optical device 71, a deformable mirror, a liquid-crystal spatial optical modulator, or the like can be used. Another appropriate optical system that can compensate for aberration of measured light may also be used. The deformable mirror reflects a light beam at an angle depending on how the mirror is deformed by an internal actuator. The deformation may be caused by a capacitance, a piezo effect, or any other appropriate factor. The liquid-crystal spatial optical modulator modulates the phase, by making use of the light distribution property of the liquid crystal, and reflects light like a mirror. The liquid-crystal spatial optical modulator may sometimes require a polarizer to be placed in the middle of the optical path. The compensating optical device 71 may not be a reflecting element but a transmitting optical element. The compensating optical device 71 compensates for aberration by deformation, for instance, depending on the output from the control block 15.

The light beams entering the compensating optical device 71 are preferably, but not limited to be, parallel. If the eye under examination 60 has no aberration, for instance, light beams reflected by the retina of the eye under examination 60 enter the compensating optical device 71 as parallel light beams. The light beams coming from the first light source also enter the compensating optical device 71 as parallel light beams.

The moving prism 72 moves in the direction of the optical axis in accordance with the output from the computer 14. The moving prism 72 is driven, for instance, by an appropriate driving section. The movement of the moving prism 72 allows a spherical component to be compensated for. The compensation can be obtained by using a spherical lens instead moving the moving prism 72.

The alignment unit 4 includes a condenser lens and an alignment light-receiving block. The alignment unit 4 guides light beams emitted from a light source and reflected from the cornea 62 of the eye under examination 60 to the alignment light-receiving block. The alignment unit may have an alignment light source or may use an appropriate light source for illuminating the eye under examination 60. In addition, when a certain pattern (such as a Placido ring) is projected by an optical system, not shown, the alignment unit 4 can guide light beams reflected from the anterior or cornea 62 of the eye under examination 60 to the alignment light-receiving block. The alignment light-receiving block can obtain an anterior image. In comparison with the first wavelength (780 nm in this embodiment), a long wavelength (940 nm, for instance) can be selected for the light beams used for alignment.

The third illumination unit (fixation unit) 5 contains an optical path to throw a visual target for the purpose of fixation or fogging of the eye under examination 60, and includes a third light source 51 (lamp, for instance), a fixation target 52, and a relay lens. The light beams coming from the third light source 51 allow the fixation target to be thrown onto the retina 61, and the eye under examination 60 can observe the image.

The optical characteristics measurement block 14-1 of the computer 14 obtains the optical characteristics including high-order aberrations of the eye under examination 60, in accordance with the output from the first light-receiving section 13. The optical characteristics measurement block 14-1 may obtain the optical characteristics from at least wavefront measurement data indicating the wavefront aberration of the eye under examination 60 as well as the output from the first light-receiving section 13.

The image data formation block 14-2 simulates the manner in which the visual target is perceived, in accordance with the optical characteristics, and calculates simulated image data or the characteristic data of the eye under examination such as an MTF indicating the manner of perception.

The memory 14-4 stores a plurality of voltage-change templates for use in an adjustment of the compensating optical device.

The correction amount determination block 14-3 selects one voltage-change template stored in the memory 14-4, determines a correction amount of the compensating optical device in accordance with the selected template, and outputs the correction amount to the control block 15. The correction amount determination block also obtains evaluation data for evaluating the quality of the retina image, on the basis of the characteristic data of the eye under examination or the simulated image data obtained for the plurality of voltage-change templates, and determines an appropriate correction amount of the compensating optical element in accordance with the evaluation data. A value indicating the degree of matching between a simulated image and a certain pattern template or an MTF can be used, for instance, as the evaluation data.

The control block 15 deforms the deformable mirror 71 in accordance with the output from the computer 14. The control block 15 also moves the moving prism 72 in the direction of the optical axis in accordance with the output from the computer 14. The movement of the moving prism 72 allows a spherical component to be corrected.

(Conjugation)

The retina 61 of the eye under examination 60, the fixation target 52 of the fixation unit 5, the first light source, and the first light-receiving section 13 conjugate. The pupil (iris) of the eye under examination 60 and the conversion member (Hartmann plate) of the first light-receiving optical block 12 conjugate. The second light source conjugates the pupil (an image is formed on the pupil) and can illuminate the most of the retina 61 evenly.

(Alignment Adjustment)

An alignment adjustment will next be described. An alignment adjustment is made mainly by the alignment unit 4.

Light beams from a light source pass through a condenser lens, a beam splitter, and the afocal lens 81, and the parallel light beams illuminate the eye under examination 60. The light beams reflected by the cornea 62 of the eye under examination 60 are returned as if they were diverging from a point positioned at half the radius of curvature of the cornea 62. The diverging light beams pass through the afocal lens 81, the beam splitter, and the condenser lens, and the alignment light-receiving block receives the light beams as a spot image.

If the spot image on the alignment light-receiving block is not on the optical axis, the retina observation apparatus is moved up and down and side to side so that the spot image comes on the optical axis. When the spot image is brought onto the optical axis, an alignment adjustment is completed. A light source, which is not shown, for illuminating the cornea 62 of the eye under examination 60 forms an image of the eye under examination 60 on the alignment light-receiving block. This image may also be used in an alignment adjustment to align the center of the pupil with the optical axis.

(Compensating Optical Device 71)

Figure 2:
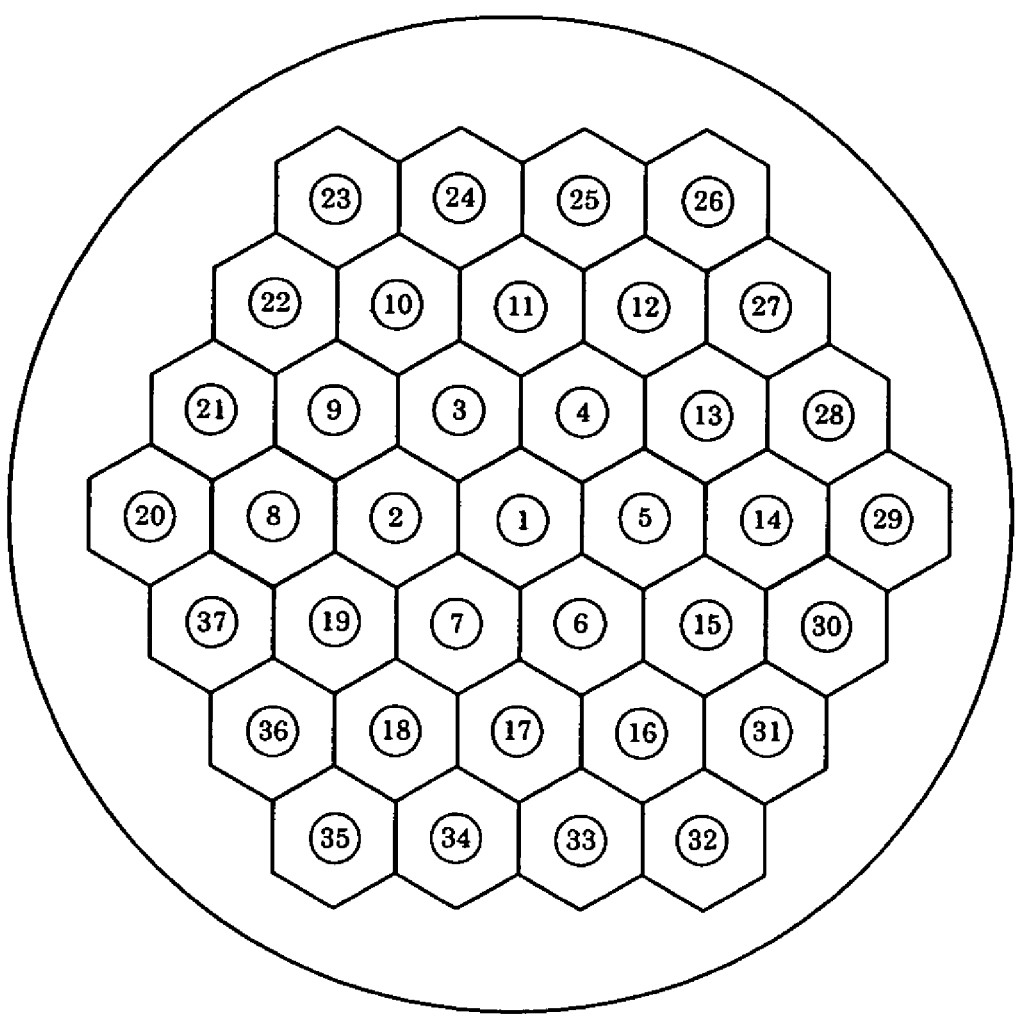
FIG. 2 is a view showing the configuration of a deformable mirror.

FIG. 2 is a view showing the configuration of the compensating optical device 71. If a deformable mirror having a neatly arranged group of elements is used, the deformable mirror is deformed by the movement of each element caused by its actuator. Each element is assigned beforehand an element number for identifying the element. The control block 15 drives each element by means of the corresponding actuator in accordance with a voltage value for the corresponding element number output by the computer 14. The number of elements is not limited to the number shown in the figure and can be any appropriated number. Element numbers not shown in the figure can be assigned. Besides the element numbers, text, coordinates, and any other appropriate identification information that can identify each element can be used.

FIG. 3 shows the format of a reference voltage table for storing a reference voltage of a voltage change. A reference voltage for changing the voltage applied to the element is stored in association with each element number of the compensating optical device 71. The computer 14 determines a voltage value to be applied to the compensating optical device 71 in accordance with the reference voltage stored here and a voltage change given by a voltage-change template, which will be described later, and outputs the value to the control block 15. The reference voltage table stores, for instance, a value of the voltage applied to the compensating optical device 71 before the correction amount is adjusted in accordance with the voltage change template. The computer 14 also updates the voltage value to a new value after the correction amount adjustment.

FIG. 4 shows the format of a table of concentric templates. The table of FIG. 4 shows that nine templates are stored for the compensating optical device 71 having 37 elements. Each template stores a value of voltage change corresponding to an element number. Generally speaking, elements near the center of the compensating optical device 71 have great effects on the picture quality, so that larger voltage changes can be specified inside in the concentric templates. This embodiment has a template with all voltage changes specified to zero. This template makes it possible to compare evaluation data without voltage change and evaluation data with voltage changes, for instance.

FIG. 5 shows the format of a table of symmetric templates. Each template stores values of voltage change in association with element numbers. In the symmetric template, symmetric values of voltage change can be specified about the center of the compensating optical device 71. The symmetric template may also have symmetric values of voltage change about the x axis, the y axis, or any other axis.

FIG. 6 shows the format of a table of asymmetric templates. Each template stores values of voltage change in association with element numbers. In the asymmetric template, asymmetric values of voltage change can be specified about the center or an axis.

The number of templates and the number of elements are not necessarily the numbers shown in FIGS. 4 to 6, and any number of templates or elements can be included. A required value of voltage change can be specified.

FIG. 7 shows a format of template matching, including matching values. A matching value obtained by template matching, which will be described later, a value of voltage applied to each element of the compensating optical device 71 used for the measurement, and a template number are stored in association with one another. MTF and other data may be stored instead of the matching value, in association with a template number. The value of voltage applied to each element may be omitted. In that case, the computer 14 can calculate the value of voltage applied to each element of the compensating optical device 71, with reference to the reference voltage table and a voltage-change template having the corresponding template number.

2. Zernike Analysis

Next, a Zernike analysis will be described. A generally known method of calculating Zernike coefficients $C_i^{2j-i}$ from Zernike polynomials will be described. The Zernike coefficients $C_i^{2j-i}$ are important parameters for grasping the optical characteristic of the subject eye 60 on the basis of inclination angles of the light fluxes obtained by the first light receiving part 13 through the conversion member, for example Hartmann plate.

Wavefront aberrations W(X, Y) of the subject eye 60 are expressed using the Zernike coefficients $C_i^{2j-i}$ and the Zernike polynomials $Z_i^{2j-i}$ by the following expression.

$$W(X, Y) = \sum_{i=0}^{n} \sum_{j=0}^{i} c_i^{2j-i} Z_i^{2j-i}(X, Y)$$

Where, (X, Y) denotes vertical and horizontal coordinates of the Hartmann plate.

Besides, with respect to the wavefront aberrations W(X, Y), when the horizontal and vertical coordinates of the first light receiving part 13 are denoted by (x, y), a distance between the Hartmann plate and the first light receiving part 13 is denoted by f, and a movement distance of a point image received by the first light receiving part 13 is denoted by ($\Delta$x, $\Delta$y), the following expression is established.

$$\frac{\partial W(X, Y)}{\partial X} = \frac{\Delta x}{f}$$
$$\frac{\partial W(X, Y)}{\partial Y} = \frac{\Delta y}{f}$$

Where, the Zernike polynomials $Z_i^{2j-i}$ are expressed by the following numerical expressions. (More specifically expressions, for example, see JP-A-2002-209854.)

$$Z_n^m = R_n^m(r) \left\{ \begin{matrix} \sin \\ \cos \end{matrix} \right\} \{m\theta\}$$
$$m > 0 \quad \sin$$
$$m \leq 0 \quad \cos$$

$$R_n^m(r) = \sum_{S=0}^{(n-m)/2} (-1)^S \frac{(n-S)!}{S!\{\frac{1}{2}(n-m)-S\}!\{\frac{1}{2}(n+m)-S\}!} r^m$$

Incidentally, with respect to the Zernike coefficients $C_i^{2j-i}$, specific values can be obtained by minimizing the squared error expressed by the following numerical expression.

$$S(x) = \sum_{i=1}^{data\ number} \left[ \left\{ \frac{\partial W(X_i, Y_i)}{\partial X} - \frac{\Delta x_i}{f} \right\}^2 + \left\{ \frac{\partial W(X_i, Y_i)}{\partial Y} - \frac{\Delta y_i}{f} \right\}^2 \right]$$

Where, W(X, Y): wavefront aberrations, (X, Y): Hartmann plate coordinates, ($\Delta$x, $\Delta$y): a movement distance of a point image received by the first light receiving part 13, f: a distance between the Hartmann plate and the first light receiving part 13.

The computer 14 calculates the Zernike coefficients $C_i^{2j-i}$, and uses this to obtain eye optical characteristics such as spherical aberrations, coma aberrations, and astigmatism aberrations. The computer 14 calculates aberration quantities $RMS_i^{2j-i}$ using the Zernike coefficients $C_i^{2j-i}$ by the following numerical expression.

$$RMS_i^{2j-i} = \sqrt{\frac{\varepsilon_i^{2j-i}}{2(i+1)}} c_i^{2j-i}$$
$$(\varepsilon_i^{2j-i} = 2(2j = i), \quad \varepsilon_i^{2j-i} = 1(2j \neq i))$$

3. Flow Charts

Figure 8:
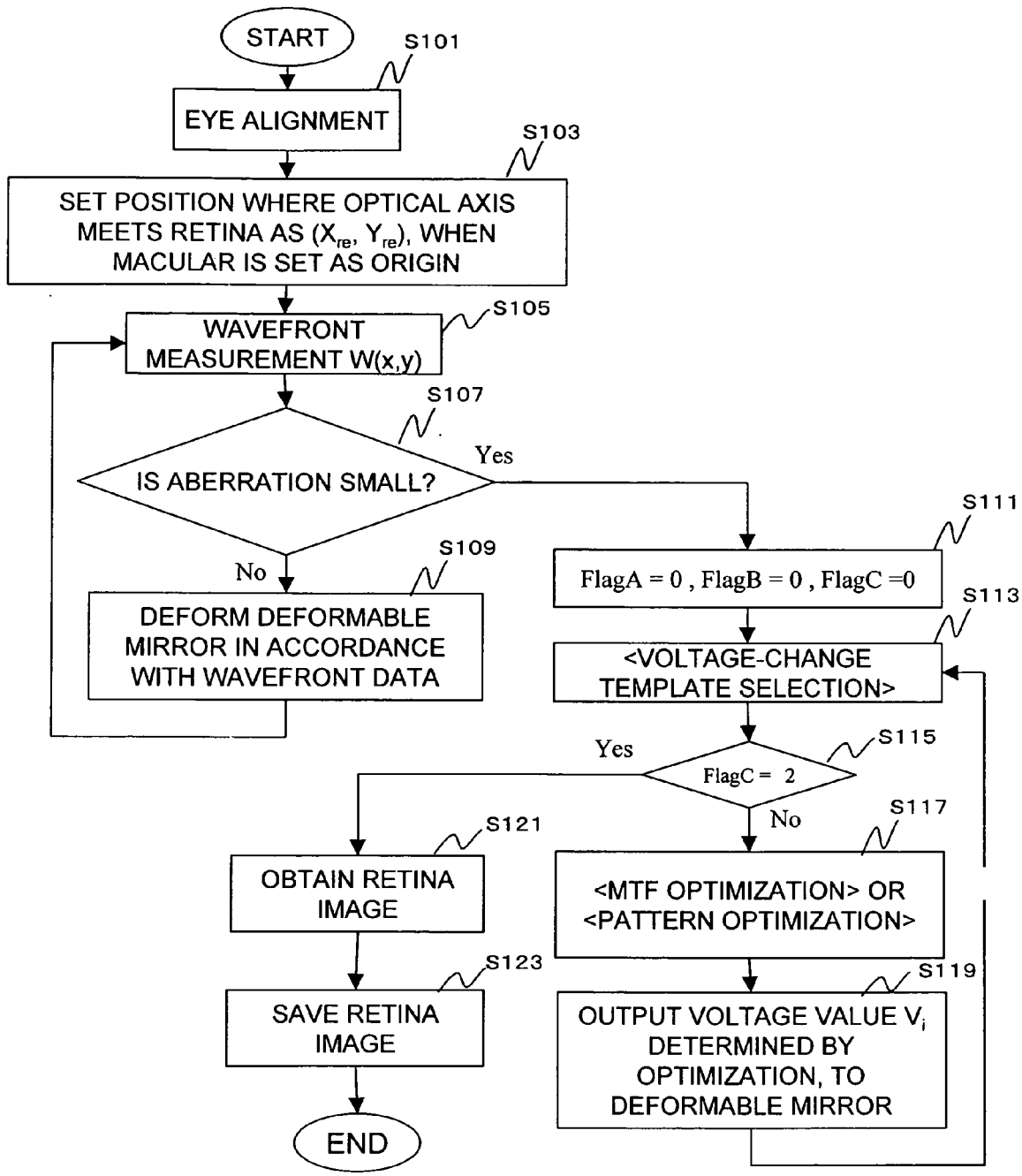
FIG. 8 shows a flow chart for retina observation.

FIG. 8 shows a flow chart for retina observation. The retina observation apparatus first performs alignment of the eye under examination 60 (S101).

The computer 14 (arithmetic logical unit, for instance) specifies a macular as an origin and a position where the optical axis from the first light source meets the retina 61 as ($X_{re}$, $Y_{re}$) (S103). The computer 14 can obtain, for instance, an retina image from the second light-receiving section and can detect the positions of the macular and the point where the optical axis meets the retina 61 through image processing. The position of the macular can be detected, for example, by a normalized correlation method, with reference to a macular template created and stored beforehand in the memory. The computer 14 may also display an obtained image on the display block and may allow the operator of the retina observation apparatus to specify the positions of the macular and the point where the optical axis meets the retina 61 by using a pointing device or another appropriate input device.

The computer 14 then measures wavefront aberration of the eye under examination 60 in accordance with the signal from the first light-receiving section 13 (S105). The computer 14 judges whether the measured aberration is smaller than a predetermined threshold (S107). The computer 14 can, for instance, calculate an aberration amount $RMS_i^{2j-i}$ from the Zernike coefficient $C_i^{2j-i}$ obtained in step S105 and judge whether the aberration amount RMS is smaller than the threshold.

If the aberration exceeds the threshold (S107), the computer 14 deforms the deformable mirror 71 to cancel out the aberration in accordance with the measured wavefront aberration (wavefront data) (S109). For example, the computer 14 determines a value of voltage applied to each element of the compensating optical device 71 in accordance with the measured wavefront aberration, and outputs the determined value of voltage to the control block 15. The computer 14 also stores the output voltage value in association with the element number in the reference voltage table provided in the memory. The computer 14 then returns to the processing of step S105.

If the aberration amount RMS is smaller than the threshold (S107), the computer 14 initializes flags (S111). For instance, the computer 14 resets flags A, B, and C to zero. The flags will be described in further detail with another flow chart.

The computer 14 next selects a voltage-change template (S113). For instance, the computer 14 selects a concentric template, a symmetric template, or an asymmetric template, in accordance with either or both of the flags and the aberration amount. The selection of a template will be described later in further detail.

The computer 14 checks whether flag C is 2 (S115). If flag C is not 2 (S115), the computer 14 performs MTF optimization or pattern optimization (S117). The computer 14 changes the value of voltage applied to the deformable mirror 71 in accordance with the voltage-change template selected in step S113, and obtains a value of voltage $V_i$ that maximizes MTF or the matching value of the simulated retina image of a certain pattern and a pattern template. The MTF optimization and pattern optimization will be described later in further detail.

The computer 14 outputs the value of voltage $V_i$ obtained in step S117 to the deformable mirror 71 (S119). The computer 14 measures wavefront aberration after a certain period of time has passed since the voltage value is output, in consideration of a period of deformation of the deformable mirror 71. The computer 14 may read wavefront data measured and stored in association with the value of voltage $V_i$ from the memory, instead of measuring wavefront aberration. The computer 14 then returns to the processing of step S113, selects a voltage-change template, and repeats the processing of step S115 and below.

If it is found that flag C is 2 in step S115, the computer 14 obtains an retina image from the second light-receiving section 32 (S121). The computer 14 stores the obtained retina image in the memory (S123) and ends the processing.

Figure 9:
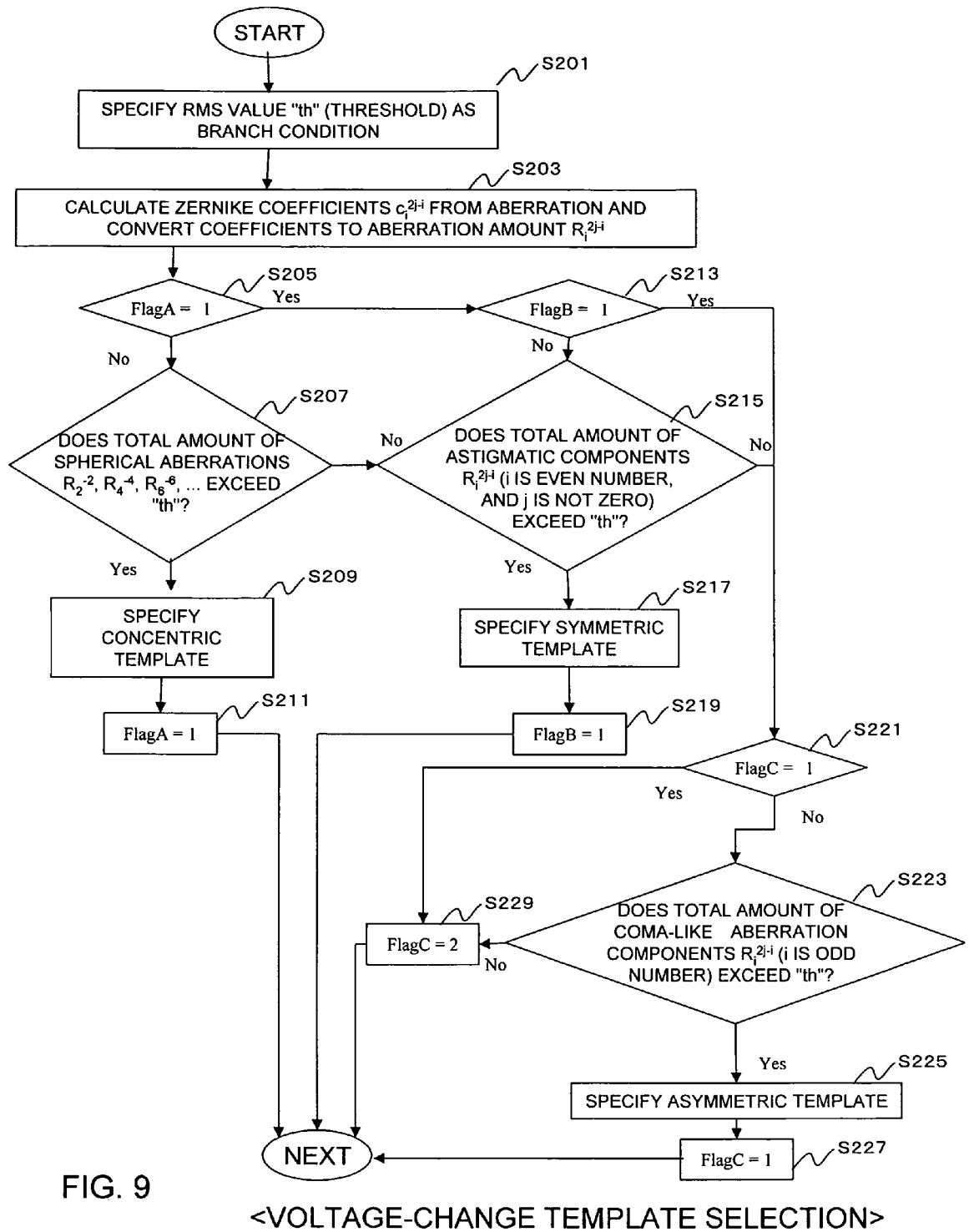
FIG. 9 shows a flow chart for selecting a voltage-change template.

FIG. 9 shows a flow chart for selecting a voltage-change template.

The computer 14 first specifies a threshold "th" of the RMS value as a condition for a branch (S201). The computer 14 sets the value of the threshold "th" to a very small value of aberration (such as 0.1). The computer 14 calculates Zernike coefficient $c_i^{2j-i}$ from the aberration and converts the coefficient to an aberration amount $R_i^{2j-i}$ (S203). The aberration amount $R_i^{2j-i}$ can be obtained by the following expression:

$$R_i^{2j-i} = \frac{\varepsilon_i^{2j-i}}{2(i+1)}(c_i^{2j-i})^2$$

$$(\varepsilon_i^{2j-i} = 2(2j=i), \quad \varepsilon_i^{2j-i} = 1(2j \neq i))$$

The computer 14 may also use the RMS obtained by expression 6 instead of the expression indicated above, as $R_i^{2j-i}$.

The computer 14 checks whether flag A is 1 (S205). If flag A is 1 (S205), the computer 14 goes to step S213. If flag A is not 1 (S205), the computer 14 checks whether the total amount of spherical aberrations $R_2^{-2}$, $R_4^{-4}$, $R_6^{-6}$, . . . exceeds the threshold "th" (S207). If Yes in step S207, the computer 14 specifies a concentric template as a voltage-change template (S209). The computer 14 also sets flag A to 1 (S211), completes the selection of the voltage-change template, and goes to step S115 in FIG. 8. If No in step S207, the computer 14 returns to the processing of step S215.

The computer 14 checks whether flag B is 1 (S213). If flag B is 1 (S213), the computer goes to step S221. If flag B is not 1 (S213), the computer goes to step S215.

The computer 14 checks whether the total amount of $R^{i2j-i}$ (i is an even number, and j is not zero) corresponding to the astigmatic component exceeds the threshold "th" (S215). If Yes in step S215, the computer 14 specifies a symmetric template as a voltage-change template (S217). The computer 14 also sets flag B to 1 (S219) and completes the selection of the voltage-change template. If No in step S215, the computer 14 goes to step S221.

The computer checks whether flag C is 1 (S221). If flag C is 1 (S221), the computer 14 goes to step S229. If flag C is not 1 (S221), the computer 14 checks whether the total amount of $R_i^{2j-i}$ (i is an odd number) corresponding to a coma-like aberration component exceeds the threshold "th" (S223). If Yes in step S223, the computer 14 specifies an asymmetric template as a voltage-change template (S225). The computer 14 also sets flag C to 1 (S227) and completes the selection of the voltage-change template.

If No in step S223 or if it is found in step S221 that flag C is 1, the computer 14 sets flag C to 2 (S229) and completes the selection of the voltage-change template.

(MTF Optimization)

Figure 10:
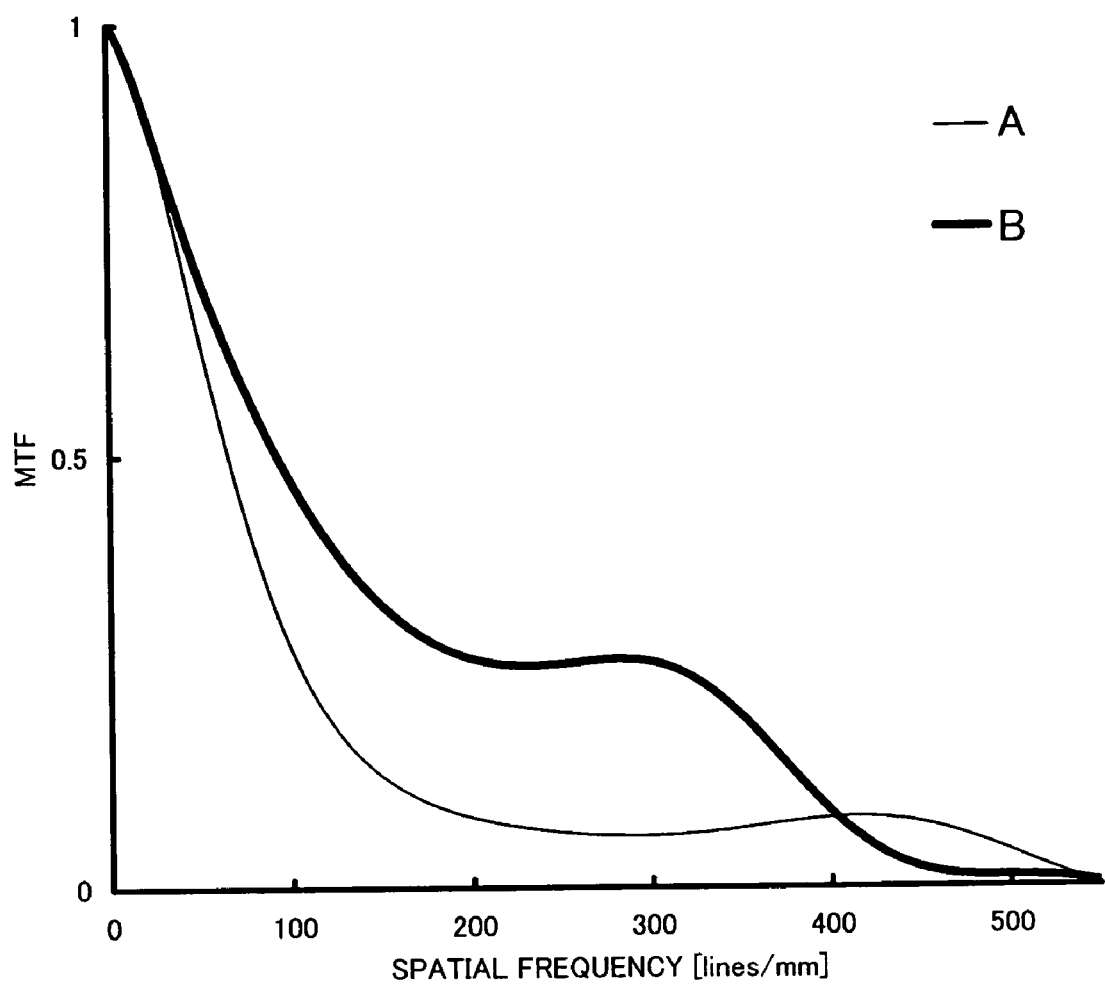
FIG. 10 is a view illustrating the best judgment in accordance with variations in MTF.

FIG. 10 is a view illustrating the determination of an optimum image in accordance with variations in MTF. With MTF, the degree of resolving power at a certain level of fineness can be checked. The figure shows a graph plotted when the deformable mirror 71 is deformed as represented by lines A and B, with the vertical axis representing the MTF value used as a measure of resolving power and the horizontal axis representing the spatial frequency used as a measure of fineness. The unit of the spatial frequency is lines/mm or cycles/degree in most cases.

The graph shows that the RMS value of B is smaller than that of A and that the MTF value of B is higher than that of A while the spatial frequency is up to 400 lines/mm. If an image close to the diffraction limit is required as with adaptive optics, A showing a resolving power in the high-frequency region above 400 lines/mm is more preferable to B.

In this embodiment, when some different voltages are applied to deform the deformable mirror 71 in accordance with the voltage-change template, the MTF value at 500 lines/mm (value for resolving an object of approximately 2 µm) is calculated. By selecting a value of voltage that maximizes the calculated MTF, a small image can be observed.

Figure 11:
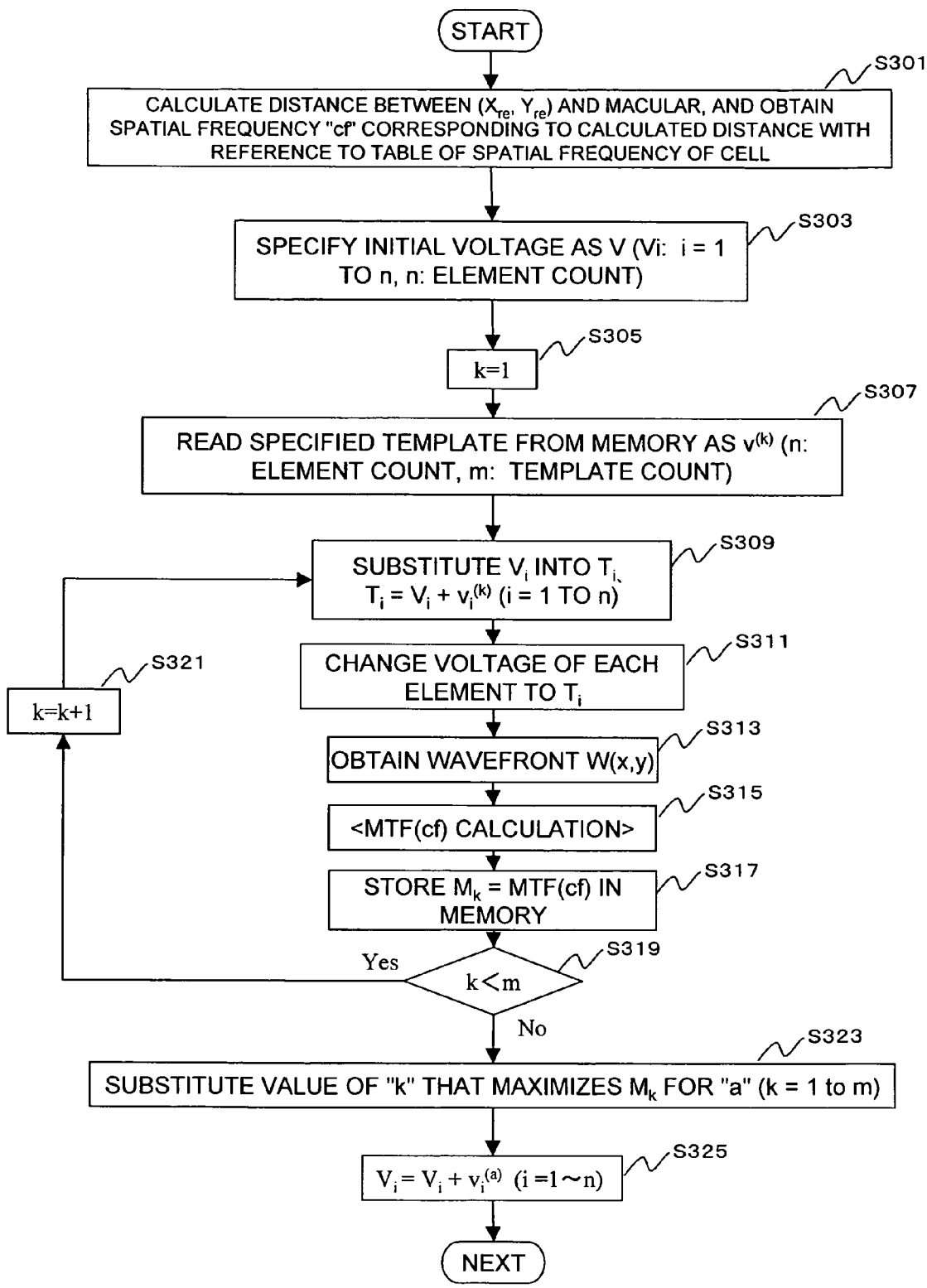
FIG. 11 shows a flow chart for MTF optimization.

FIG. 11 shows a flow chart for MTF optimization.

The computer 14 calculates the distance between the position $(X_{re}, Y_{re})$ where the optical axis of light illuminating the retina 61 of the eye under examination 60 meets the retina 61 and the macular (origin of the coordinate system), and obtains the spatial frequency cf corresponding to the calculated distance with reference to the table of the spatial frequency of the cell (S301).

Figure 12:
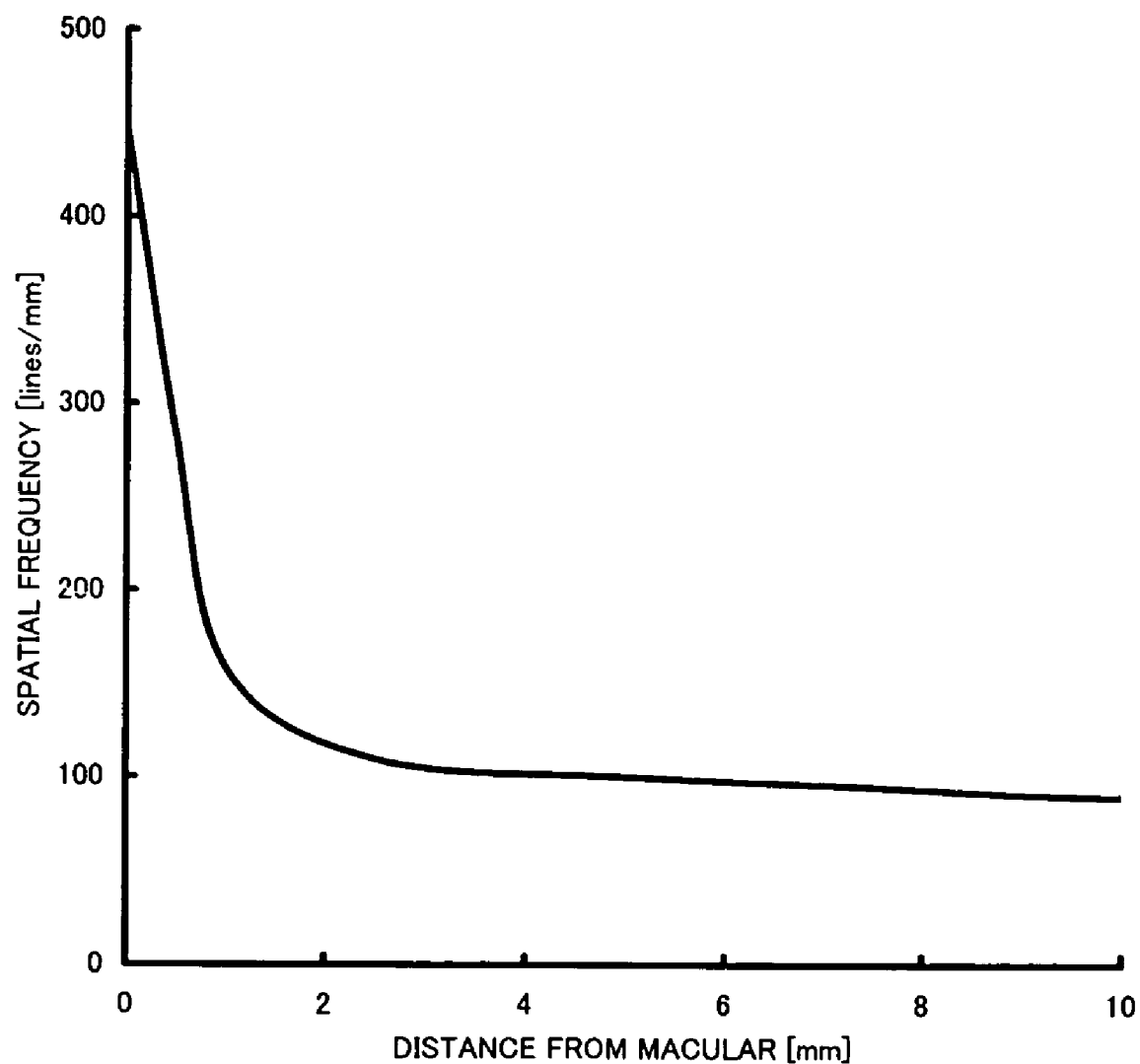
FIG. 12 is a view showing the relationship between the distance from a macular and the spatial frequency of a cell.

FIG. 12 is a view showing the relationship between the distance from the macular and the spatial frequency of the cell. For the human eye, the spatial frequency of the cell decreases as the distance from the macular increases, as shown in FIG. 12. The shown relationship may be stored in the memory as a table indicating the relationship between the distance from the macular and the spatial frequency, so that the computer 14 can read the spatial frequency cf corresponding the calculated distance from the memory. Alternatively, an approximate expression representing the relationship between the distance from the macular and the spatial frequency as shown in FIG. 12 may be stored in the memory, so that the computer 14 can calculate the spatial frequency cf corresponding to the calculated distance in accordance with the approximate expression.

Then, the computer 14 specifies the initial voltage as V (Vi: i=1 to n), where n is the number of elements of the deformable mirror 71 (S303). The computer 14 can read the voltage corresponding to each element number from the reference voltage table stored in the memory and can specify this voltage as the initial voltage V.

The computer 14 specifies a template number k to 1, for instance (S305). The template number functions as a counter for calculating the MTF of a plurality of templates.

The computer 14 reads the voltage-change template selected in step S113 as $v^{(k)}$ from the memory (S307). The computer 14 reads all the templates stored in the memory, for example, each voltage-change amount of template number 1 as $v^{(1)}$ each voltage-change amount of template number 2 as $v^{(2)}$ and so on. The computer 14 also reads the template count m from the memory. The computer 14 may count the number of read templates and specify it as a template count m, instead of reading the template count.

The computer 14 specifies voltage value $T_i$ (S309), as expressed by:

$$T_i = V_i + v_i^{(k)} (i=1 \text{ to } n)$$

The computer 14 changes the value of the voltage to be applied to each element of the deformable mirror 71 to $T_i$, and outputs $T_i$ to the control block 15 (S311). The control block 15 deforms the deformable mirror 71 by driving each element of the deformable mirror 71 in accordance with the voltage $T_i$ output from the computer 14. The computer 14 measures wavefront aberration W(x,y) after the deformable mirror 71 is deformed (after a certain period of time, for instance) (S313).

The computer 14 calculates MTF(cf) from the measured wavefront aberration (S315). MTF(cf) is an average of MTFs at all angles corresponding to the spatial frequency cf of the cell, for instance. The calculation of MTF(cf) will be described later. The computer 14 sets the calculated MTF(cf) as $M_k$ (S317). The computer 14 also stores $M_k$ in the memory in association with the template number k. The computer 14 may store the measured wavefront aberration, data based on the aberration, and the voltage $T_i$ at a certain timing, in association with the template number k.

The computer 14 checks whether the template number k is smaller than the template count m (S319). That is, the computer 14 checks whether $M_k$ has been obtained for all the templates. If the template number k is smaller than the template count m (S319), the computer 14 increments k by one (S321) and repeats the processing of step S309 and below.

If the template number k is greater than template count m (S319), the computer 14 substitutes the value of k that maximizes $M_k$ (k=1 to m) for "a" (S323). For instance, the computer 14 searches for $M_k$ having a greater value than any other $M_k$ stored in the memory, reads the corresponding template number k, and substitutes this "k" for "a".

The computer 14 specifies the voltage $V_i$ obtained by the following expression (S325):

$$V_i = V_i + v_i^{(a)} (i=1 \text{ to } n)$$

The computer 14 enters the specified $V_i$ in the reference voltage table stored in the memory. If voltages corresponding to $M_k$ have already been stored in the memory, the computer 14 may search for $M_k$ having a greater value than any other $M_k$ stored in the memory, read the greater value corresponding to this $M_k$, and specify the voltage as $V_i$ in step S323. Then, the processing of step S325 can be omitted. The computer 14 then terminates the MTF optimization and goes to step S119 in FIG. 8. The processing described above specifies the voltage $V_i$ to maximize MTF(cf).

Figure 13:
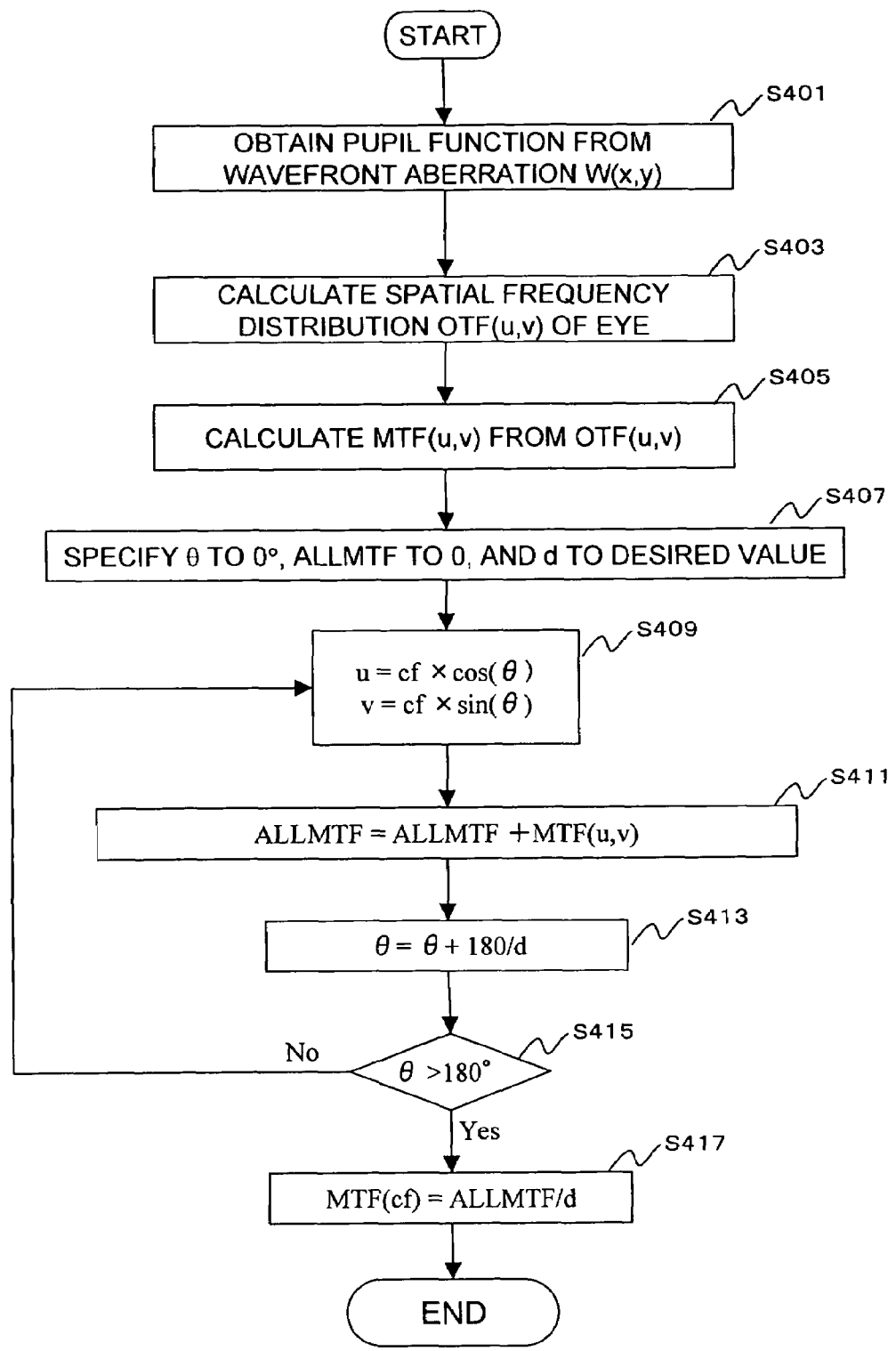
FIG. 13 shows a flow chart for MTF(cf) calculation.

FIG. 13 shows a flow chart for MTF(cf) calculation.

The computer 14 obtains pupil function f(x,y) from wavefront aberration W(x,y), as indicated below (S401):

$$f(x,y) = e^{ikw(x,y)}$$

(i: Imaginary, k: Wave vector ($2\pi/\lambda$), $\lambda$: Wavelength) The computer then calculates spatial frequency distribution OTF(u,v) of the eye in accordance with the pupil function (S403). The calculation of the spatial frequency distribution of the eye is described below.

The computer 14 first obtains a point spread function by amplitude U(u,v), through a Fourier transform of pupil function (x,y), as expressed below:

$$U(u,v) = \int\int_{-\infty}^{\infty} f(x,y) \exp\left[-\frac{i}{R}\frac{2\pi}{\lambda}(ux+vy)\right] dx\,dy$$

($\lambda$: Wavelength,

R: Distance from pupil to image point (retina), (u,v): Coordinates in a plane orthogonal to the optical axis, with reference to image point O set to origin, (x,y): Coordinates in pupil plane)

The computer 14 multiplies U(u,v) by its complex conjugate number and obtains I(u,v), a point spread function (PSF), from the following expression:

$$I(u,v) = U(u,v)U^*(u,v)$$

The computer 14 obtains OTF by normalizing PSF by means of a Fourier transform (or self-correlation) as expressed below:

$$R(r,s) = \int\int_{-\infty}^{\infty} I(u,v) e^{-i2\pi(ru+sv)} du\,dv$$

(r, s: Variables in spatial frequency domain)

$$OTF = \frac{R(r,s)}{R(0,0)}$$

The computer 14 obtains MTF(u,v) from OTF(u,v) as expressed below (S405):

$$MTF(u,v) = |OTF(u,v)|$$

The computer initializes parameters (S407). For instance, the computer specifies angle $\theta$ to 0° and ALLMTF, or the sum of MTF, to 0, and specifies a partition number "d" to a certain value (36, for instance). The partition number "d" represents the number of partitions into which an angle of 180° is divided in MTF calculation. If "d" is set to 36, angle $\theta$ can be specified in units of 5°. Any value can be specified as "d", but a multiple of 2 is preferable.

The computer 14 calculates v and v in accordance with the following expressions (S409):

$$u = cf \times \cos(\theta)$$

$$v = cf \times \sin(\theta)$$

where cf is the spatial frequency obtained in step S301.

The computer 14 obtains MTF(u,v) in accordance with u and v calculated above and obtains ALLMTF in accordance with the following (S411):

$$ALLMTF = ALLMTF + MTF(u,v)$$

The computer 14 then changes the angle $\theta$ in accordance with the following expression (S413):

$$\theta = \theta + 180/d$$

The computer 14 checks whether $\theta$ is greater than 180° (S415). If $\theta$ is smaller than 180° (S415), the computer 14 returns to step S409. If $\theta$ is greater than 180° (S415), the computer 14 calculates MTF(cf) in accordance with the following expression (S417):

$$MTF(cf) = ALLMTF/d$$

The computer than terminates the MTF(cf) calculation and goes to step S317 in FIG. 11.

(Pattern Optimization)

Figure 14:
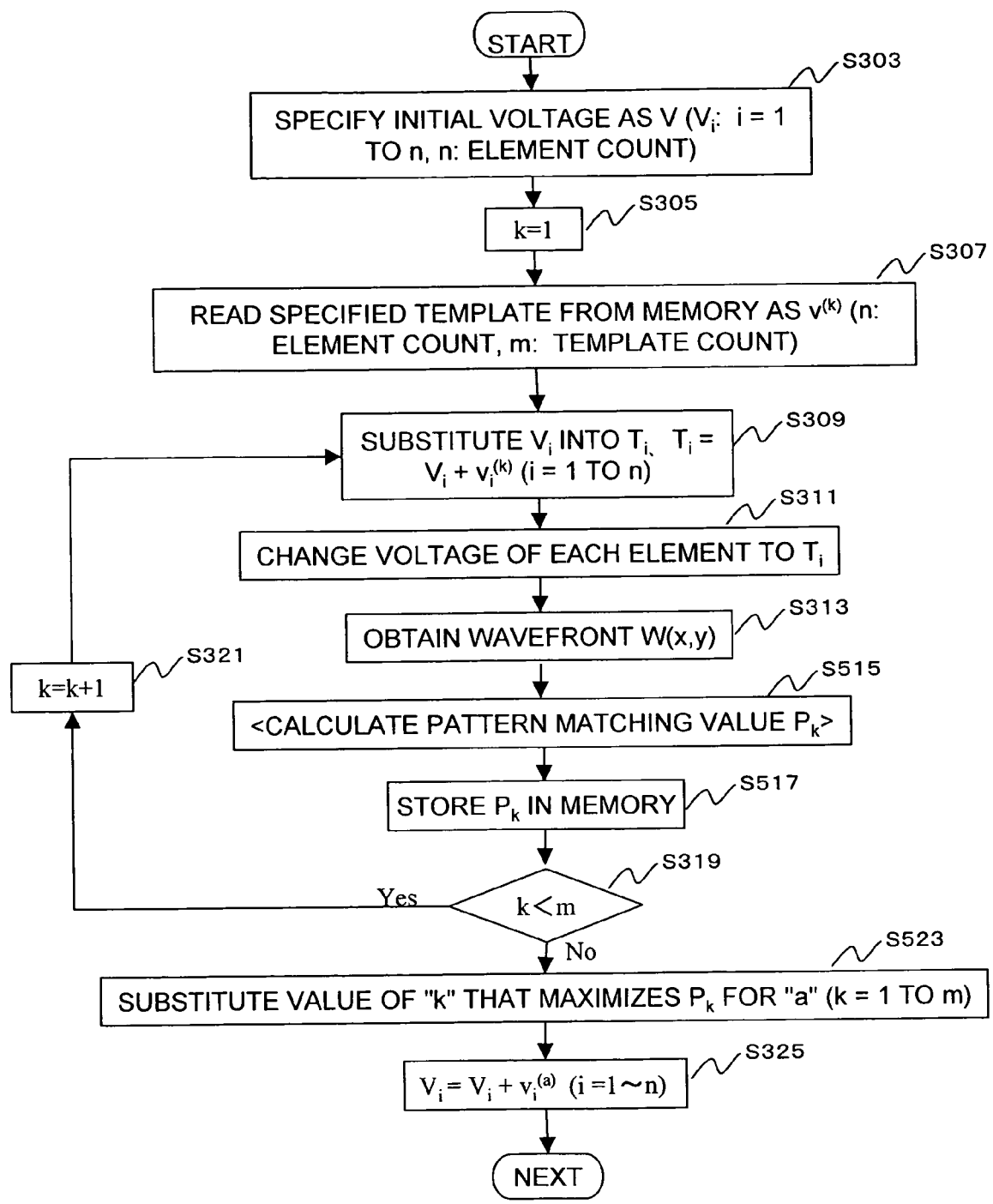
FIG. 14 shows a flow chart for pattern optimization.

FIG. 14 shows a flow chart for pattern optimization.

The computer 14 performs steps S303 to S313. Those steps have been described above, and detailed descriptions thereof will not be repeated below. The computer 14 calculates a pattern matching value $P_k$ (S515). The computer 14 simulates a retina image of a certain pattern, compares a pattern template corresponding to the pattern and the simulated retina image through pattern matching, and obtains the pattern matching value $P_k$. The specific method of obtaining the pattern matching value $P_k$ will be described later. The computer 14 stores the calculated pattern matching value $P_k$ in association with both or either of the template number k and voltage $V_i$ in the memory (S517).

The computer 14 then checks whether the template number k is smaller than the template count m (S319). If the template number k is smaller than the template count m (S319), the computer 14 increments k by one (S321) and repeats the processing of step S309 and below. If the template number k is greater than the template count m (S319), the computer 14 substitutes the value of k that maximizes $P_k$ (k=1 to m) for "a" (S523). For instance, the computer 14 searches for $P_k$ having a greater value than any other $P_k$ stored in the memory, reads the corresponding template number k, and substitutes "k" for "a"

The computer 14 performs step S325, specifies the voltage $V_i$, and adds $V_i$ to the reference voltage table stored in the memory. If voltages corresponding to $P_k$ have already been stored in the memory, the computer 14 may search for $P_k$ having a greater value than any other $P_k$ stored in the memory, read the value of voltage corresponding to this $P_k$, and specify the value as $V_i$ in step S523. Then, the processing of step S325 can be omitted. Now, the voltage $V_i$ that maximizes pattern matching value $P_k$ is specified.

Figure 15:
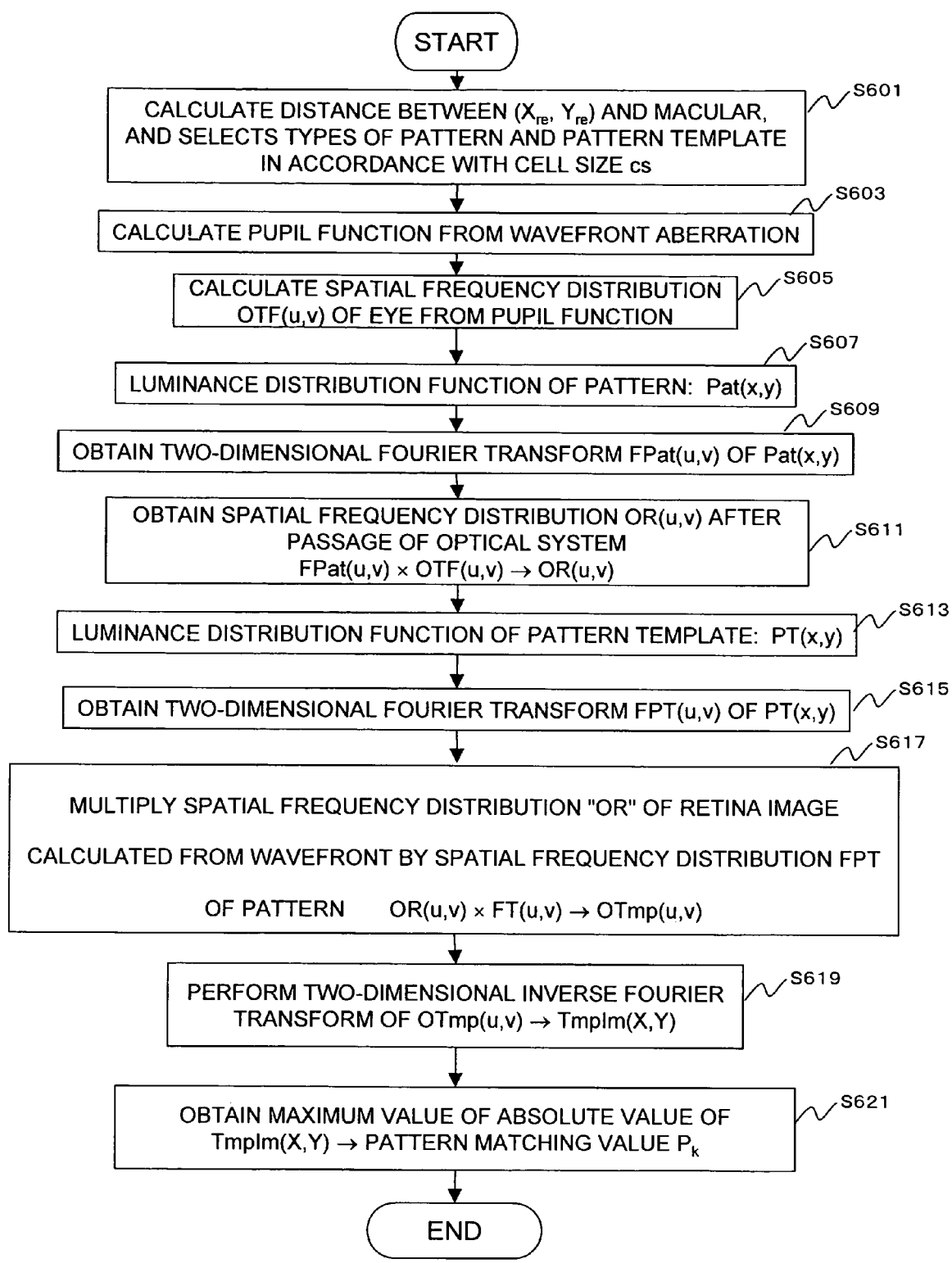
FIG. 15 shows a flow chart for calculation of pattern matching value $P_k$.

FIG. 15 shows a flow chart for calculation of pattern matching value $P_k$.

The computer 14 calculates the distance between the position $(X_{re}, Y_{re})$ where the optical axis of light illuminating the retina 61 of the eye under examination 60 meets the retina 61 and the macular, and selects the types of pattern and pattern template with reference to a table storing the relationship between the calculated distance and the type of pattern (S601).

Figure 16:
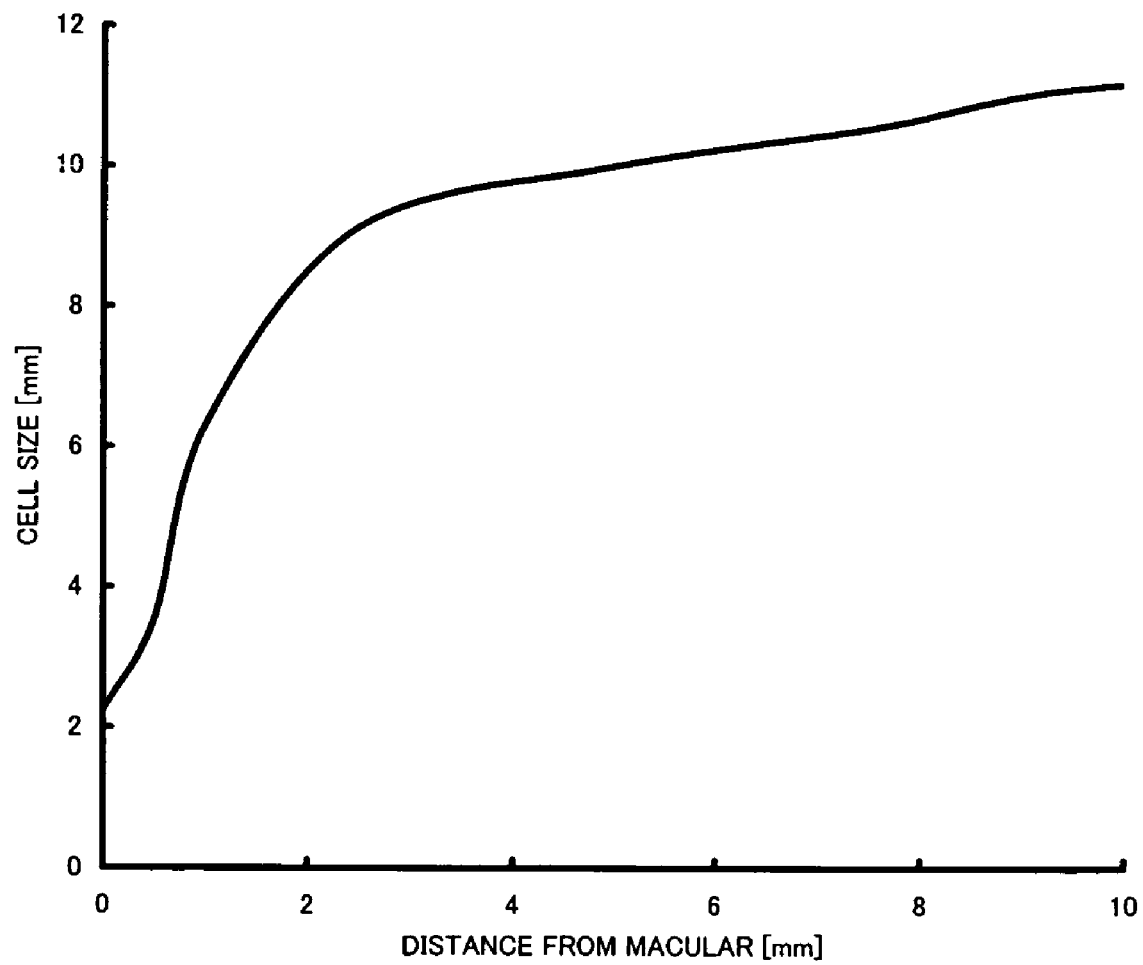
FIG. 16 is a view showing the relationship between the distance from the macular and a cell size.

FIG. 16 is a view showing the relationship between the distance from the macular and the size of the cell. As shown in the figure, the size of the cell at the retina of a human eye depends on the distance from the macular. A pattern of a size corresponding to the distance from the macular is selected through pattern matching in this embodiment.

The computer 14 calculates the distance between $(X_{re}, Y_{re})$ and the macular and obtains a cell size "cs" in accordance with the calculated distance. A table associating the distance from the macular with the cell size may be stored beforehand in the memory, so that the computer 14 can read the cell size "cs" corresponding to the calculated distance from the table. Alternatively, an approximate expression of the graph shown in FIG. 16 may be stored in the memory, so that the computer 14 can obtain the cell size based on the calculated distance in accordance with the approximate expression. The computer 14 selects the pattern original image Pat(x,y) in accordance with the obtained cell size "cs".

FIG. 17 is a view illustrating pattern original images. A line section of a pattern is assigned a pixel value of 1 and is created with a relatively smaller size than the cell size "cs". The other section of the pattern has a pixel value of 0. A desired number of patterns are created in advance, each having a different cell size "cs", and the pattern original images are stored in the memory in association with the range of the cell size "cs" identifying each pattern. The computer 14 can select a pattern corresponding to the obtained cell size "cs" with reference to the range of the cell size "cs" stored in the memory.

FIG. 18 is a view illustrating pattern template images PT(x,y). A lattice image corresponding to the cell size "cs" is created as a pattern template image corresponding to the pattern original image described above. Supposing the line section has a pixel count N1, the internal shaded section is created to have a pixel count N2 and a pixel value of –N1/N2. The pattern template image is stored in the memory in association with the pattern described above.

A pattern original image and a pattern template image can have another pattern corresponding to the cell size or any other pixel value. The pattern may not be a square lattice as described above, and a spherical object likened as a cell may be used, for instance, as a pattern. A pattern or a pattern template which has already been created and stored in the memory may not be selected, and a pattern may be created, for example, in accordance with the obtained cell size.

Back to the flow chart shown in FIG. 15, the computer 14 calculates the pupil function f(x,y) from the wavefront aberration W(X,Y) (S603), as expressed by:

$$f(x,y)=e^{ikw(X,Y)}$$

(i: Imaginary, k: Wave vector ($2\pi/\lambda$), $\lambda$: Wavelength) The computer 14 calculates a luminance distribution function Pat(x,y) of the selected pattern, with reference to the memory (S607). The computer 14 performs a two-dimensional Fourier transform of Pat(x,y) and obtains a spatial frequency distribution FPat(u,v) (S609).

The computer 14 obtains the spatial frequency distribution OTF of the eye from the pupil function, and obtains a frequency distribution OR(u,v) (of a retina image) after the passage of the optical system of the eye, by multiplying the spatial frequency distribution FPat(u,v) of the pattern and the spatial frequency distribution OTF(u,v) of the eye, as expressed below (S611):

$$FPat(u,v) \times OTF(u,v) \rightarrow OR(u,v)$$

The computer 14 calculates the luminance distribution function PT(x,y) of the pattern template with reference to the memory (S613). The computer 14 obtains a two-dimensional Fourier transform FPT(u,v) of PT(x,y) (S615).

The computer 14 obtains OTmp(u,v) by multiplying the spatial frequency distribution OR(u,v) of the retina image calculated from the wavefront and the spatial frequency distribution FPT(u,v) of the pattern (S617).

$$OR(u,v) \times FT(u,v) \rightarrow OTmp(u,v)$$

The computer 14 then performs a two-dimensional inverse Fourier transform of OTmp(u,v) to obtain TmpIm(X,Y) (S619). The computer 14 obtains the maximum value of the absolute value of TmpIm(X,Y) and uses it as the pattern matching value $P_k$ (S621). The computer 14 terminates the calculation of the patter matching value and returns to step S517 shown in FIG. 14.

4. Example of Comparison

FIG. 19 is a view comparing an image obtained through pattern optimization with other images. The figure shows a wavefront aberration, a simulated Landolt's ring image, a simulated moiréimage, and RMS when no correction is made, when correction is made to decrease the aberration amount RMS (RMS optimization), and when correction is made through pattern optimization of this embodiment. The figure indicates that the image of pattern optimization can be perceived better although pattern optimization provides a greater RMS than RMS optimization.

5. Appendix

The retina observation apparatus and retina observation system of the present invention can be provided by an retina observation program for executing the processing by a computer, a computer-readable recording medium storing the retina observation program, a program product that can be loaded into the internal memory of the computer, including the retina observation program, a computer such as a server containing the program, or the like.

The optical characteristics measurement block 14-1 obtains the optical characteristics of the eye under examination 60, from the output of the first light-receiving optical block 12 shown in FIG. 1. The configuration can be changed to obtain the optical characteristics from wavefront measurement data including wavefront aberration from an appropriate optical block or apparatus.

INDUSTRIAL APPLICABILITY

According to this invention, it can be adjusted the correction to be made by the compensating optical device so that the quality of the retina image is improved, and obtained an appropriate amount of correction. According to this invention, it can be obtained an appropriate amount of correction for improving the picture quality in accordance with a value obtained from pattern matching between the manner in which a visual target is perceived by an eye under examination and a certain pattern template, or an MTF (modulation transfer function). Furthermore, according to this invention, it can be provided an retina image corrected by an appropriate correction amount. According to this invention, it can be improved the quality of the retina image by means of a voltage-change template provided to adjust the correction amount of the compensating optical device. According to this invention, it can be evaluated the image quality in consideration of the size of the retina cell and to enable observations up to the cell level.

The invention claimed is:

1. An retina observation apparatus comprising:
   an retina illumination unit for illuminating the retina of an eye under examination for the purpose of observation;
   a compensating optical section for correcting a image of the retina formed by the illumination of the retina illumination unit by a given amount of correction;
   an retina-image-forming optical block for forming an retina image by receiving the image of the retina corrected by the compensating optical section;
   an retina-image-light-receiving section for receiving the retina image formed by the retina-image-forming optical block;
   a wavefront measurement block for obtaining wavefront measurement data including at least either or both of a wavefront aberration of the eye under examination and the aberration corrected by the compensating optical section;
   an optical characteristics measurement block for obtaining optical characteristics including a high-order aberration of the eye under examination, from the wavefront measurement data given by the wavefront measurement block;
   an image data formation block for simulating the manner in which a visual target is perceived on the retina, in accordance with the optical characteristics obtained by the optical characteristics measurement block, and calculating data indicating the manner of perception;
   a storage block for storing a plurality of voltage-change templates for use in an adjustment of the compensating optical section; and
   a correction amount determination block for selecting a voltage-change template stored in the storage block, determining an amount of correction to be made by the compensating optical section in accordance with the template and outputting the amount of correction to the compensating optical section, obtaining evaluation data for evaluating the quality of the image in accordance with the data indicating the manner in which the visual target is perceived, obtained by the image data formation block, in consideration of the amount of correction based on the plurality of voltage-change templates, determining an appropriate amount of correction to be made by the compensating optical section in accordance with the evaluation data, and outputting the appropriate amount of correction to the compensating optical section.

2. An retina observation apparatus according to claim 1, wherein the compensating optical section includes adaptive optics having a plurality of movable mirrors or spatial optical modulators.

3. An retina observation apparatus according to claim 2, wherein the compensating optical section further includes either or both of a moving prism configured to be capable of moving in the direction of the optical axis and a spherical lens section.

4. An retina observation apparatus according to claim 1, wherein the wavefront measurement block comprises:
   a point-image-projecting optical block for projecting a point image onto the retina of the eye under examination;
   a point-image-light-receiving optical block for forming a point image through a splitting element for splitting a light beam sent by the point-image-projecting optical block and reflected by the retina of the eye under examination into at least seventeen light beams; and
   a point-image-light-receiving section for receiving the point image formed by the point-image-light-receiving optical block; and
   the optical characteristics measurement block is configured to obtain the output from the point-image-light-receiving section as the wavefront measurement data and determine the optical characteristics including the high-order aberration of the eye under examination.

5. An retina observation apparatus according to claim 1, wherein the voltage-change templates stored in the storage block include one or more of a concentric template having a greater voltage change specified near the center of the compensating optical section than in the periphery, a symmetric template having voltage changes specified symmetrically with respect to the center or a desired axis of the compensating optical section, and an asymmetric template having voltage changes specified asymmetrically with respect to the center or a desired axis of the compensating optical section.

6. An retina observation apparatus according to claim 5, wherein the correction amount determination block selects a concentric template if an amount of spherical aberration exceeds a certain level, selects a symmetric template if an astigmatic component exceeds a certain level, or selects an asymmetric template if a coma-like aberration component exceeds a certain level, in accordance with the amount of aberration obtained by the optical characteristics measurement block.

7. An retina observation apparatus according to claim 1, wherein the image data formation block simulates the manner in which a certain visual target is perceived on the retina and obtains simulated image data; and the correction amount determination block is configured to compare pattern template data corresponding to the visual target and the simulated image data through pattern matching and determine an appropriate amount of correction in accordance with a value indicating the degree of matching.

8. An retina observation apparatus according to claim 7, wherein the correction amount determination block is configured to perform a two-dimensional Fourier transform of a luminance distribution function of the pattern template data corresponding to the visual target used for simulation, carry out pattern matching by multiplying the result of the Fourier transform by the spatial frequency distribution of the simulated image data, and determine whether the correction amount is appropriate in accordance with a value indicating the degree of matching.

9. An retina observation apparatus according to claim 8, wherein the image data formation block is configured to calculate a spatial frequency distribution of the eye in accordance with the wavefront aberration, perform a two-dimensional Fourier transform of a luminance distribution function of a certain visual target, and obtain the spatial frequency distribution of simulated image data by multiplying the spatial frequency distribution of the eye by the result of the Fourier transform.

10. An retina observation apparatus according to claim 7, wherein the image data formation block is configured to calculate the distance between a point where the optical axis of light illuminating the retina of the eye under examination meets the retina and a macular, and use a visual target corresponding to the calculated distance.

11. An retina observation apparatus according to claim 1, wherein the image data formation block calculates MTF (modulation transfer function) data as data indicating the manner of perception of a image, in accordance with the optical characteristics obtained by the optical characteristics measurement block; and the correction amount determination block is configured to determine an appropriate amount of correction in accordance with the calculated MTF data.

12. An retina measurement apparatus according to claim 11, wherein the correction amount determination block calculates the distance between a point where the optical axis of light illuminating the retina of the eye under examination meets the retina and a macular, obtains a spatial frequency corresponding to the calculated distance, with reference to data indicating the relationship between the distance from the macular and the spatial frequency, stored beforehand in the storage block, calculates an MTF value corresponding to the spatial frequency, on the basis of the obtained spatial frequency and the MTF data calculated by the image data formation block, and determines an appropriate amount of correction in accordance with the MTF value.

13. An retina observation apparatus according to claim 1, wherein the correction amount determination block determines an amount of correction to start correction from weak correction side.

14. An retina observation method comprising:

a step of illuminating the retina of an eye under examination for the purpose of observation;

a step of correcting a image of the retina formed by the illumination, by a given amount of correction;

a step of forming an retina image by receiving the corrected image of the retina;

a step of measuring wavefront measurement data indicating at least either or both of a wavefront aberration of the eye under examination and the aberration to be corrected;

a step of obtaining optical characteristics including a high-order aberration of the eye under examination, from the wavefront measurement data;

a step of calculating data indicating the manner of perception, by simulating the manner in which a image is perceived on the retina, in accordance with the obtained optical characteristics;

a step of determining and outputting the amount of correction in accordance with the template which is selected a voltage-change template for use in an adjustment of an amount of correction and;

a step of determining an appropriate amount of correction in accordance with the evaluation data which is obtained for evaluating the quality of the image in accordance with the data indicating the manner in which the image is perceived, in consideration of the amount of correction based on a plurality of voltage-change templates and a step of outputting the amount of correction determined in the step of determining.

15. An retina observation method according to claim 14, wherein a correction is made by adaptive optics having a plurality of movable mirrors or spatial optical modulators, in the step of correcting.

16. An retina observation method according to claim 15, wherein a further correction is made by both or either of a moving prism configured to be capable of moving in the direction of the optical axis and a spherical lens section, in the step of correcting.

17. An retina observation method according to claim 14, wherein the step of measuring comprises steps of:

projecting a point image onto the retina of the eye under examination;

forming a point image through a splitting element for splitting a light beam reflected by the retina of the eye under examination into at least seventeen light beams; and receiving the formed point image; and the received point image data is obtained as the wavefront measurement data indicating at least a wavefront aberration of the eye under examination, and the optical characteristics including the high-order aberration of the eye under examination are obtained, in the step of determinating.

18. An retina observation method according to claim 14, wherein a voltage-change template to be selected in the step of outputting is one or more of a concentric template having a greater voltage change specified near the center of the compensating optical section for correcting the image of the retina than in the periphery, a symmetric template having voltage changes specified symmetrically with respect to the center or a desired axis of the compensating optical section, and an asymmetric template having voltage changes specified asymmetrically with respect to the center or a desired axis of the compensating optical section.

19. An retina observation method according to claim 18, wherein a template to be selected in accordance with the calculated amount of aberration in the step of outputting is a concentric template if an amount of spherical aberration exceeds a certain level, a symmetric template if an astigmatic component exceeds a certain level, or an asymmetric template if a coma-like aberration component exceeds a certain level.

20. An retina observation method according to claim 14, wherein the manner in which a certain visual target is perceived on the retina is simulated, and simulated image data is obtained in the step of calculating; and the step of determing comprises steps of:
comparing pattern template data corresponding to the visual target and the simulated image data through pattern matching; and
judging whether the amount of correction is appropriate, from the value indicating the degree of matching.

21. An retina observation method according to claim 20, wherein a two-dimensional Fourier transform is performed on a luminance distribution function of the pattern template data corresponding to the visual target used for simulation, pattern matching is carried out by multiplying the result of the Fourier transform by the spatial frequency distribution of the simulated image data, and whether the correction amount is appropriate is judged from the value indicating the degree of matching, in the step of determining.

22. An retina observation method according to claim 21, wherein a spatial frequency distribution of the eye is calculated in accordance with the wavefront aberration, a two-dimensional Fourier transform is performed on a luminance distribution function of a certain visual target, and the spatial frequency distribution of simulated image data is obtained by multiplying the spatial frequency distribution of the eye by the result of the Fourier transform, in the step of calculating.

23. An retina observation method according to claim 20, wherein the distance between a point where the optical axis of light illuminating the retina of the eye under examination meets the retina and a macular is calculated, and a visual target corresponding to the calculated distance is used to simulate the manner of perception, in the step of calculating.

24. An retina observation method according to claim 14, wherein MTF (modulation transfer function) data is calculated as data indicating the manner of perception of a image in accordance with the obtained optical characteristics in the step of calculating; and an appropriate amount of correction is determined in accordance with the calculated MTF data in the step of determining.

25. An retina measurement method according to claim 24, wherein the distance between a point where the optical axis of light illuminating the retina of the eye under examination meets the retina and a macular is calculated, a spatial frequency corresponding to the calculated distance is obtained with reference to data indicating the relationship between the distance from the macular and the spatial frequency, stored beforehand in the storage block, an MTF value corresponding to the spatial frequency is calculated on the basis of the obtained spatial frequency and the MTF data calculated by the image data formation block, and an appropriate amount of correction is determined in accordance with the MTF value, in the step of determining.

26. An retina observation method according to claim 14, wherein an amount of correction is determined to start correction from weak correction side, in the second step of outputting.

* * * * *